US009631243B2

(12) United States Patent
Major et al.

(10) Patent No.: US 9,631,243 B2
(45) Date of Patent: Apr. 25, 2017

(54) METHODS AND COMPOSITIONS FOR IDENTIFYING JC VIRUS

(71) Applicant: The United States of America, as represented by the Secretary, Department of Health and Human Services, Washington, DC (US)

(72) Inventors: Eugene Major, Darnestown, MD (US); Caroline Ryschkewitsch, Chevy Chase, MD (US)

(73) Assignee: THE UNITED STATES OF AMERICA, AS REPRESENTED BY THE SECRETARY, DEPARTMENT OF HEALTH AND HUMAN SERVICES, Washington, DC (US)

( * ) Notice: Subject to any disclaimer, the term of this patent is extended or adjusted under 35 U.S.C. 154(b) by 102 days.

(21) Appl. No.: 14/408,919

(22) PCT Filed: Jun. 17, 2013

(86) PCT No.: PCT/US2013/046158
§ 371 (c)(1),
(2) Date: Dec. 17, 2014

(87) PCT Pub. No.: WO2013/192100
PCT Pub. Date: Dec. 27, 2013

(65) Prior Publication Data
US 2015/0176089 A1    Jun. 25, 2015

Related U.S. Application Data

(60) Provisional application No. 61/661,289, filed on Jun. 18, 2012.

(51) Int. Cl.
*C12Q 1/68* (2006.01)
*C12Q 1/70* (2006.01)

(52) U.S. Cl.
CPC ........ *C12Q 1/701* (2013.01); *C12Q 2600/112* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| | | |
|---|---|---|
| 5,427,930 A | 6/1995 | Birkenmeyer et al. |
| 5,744,311 A | 4/1998 | Fraiser et al. |
| 6,025,134 A | 2/2000 | Sooknanan |
| 6,033,881 A | 3/2000 | Himmler et al. |
| 2009/0075274 A1 | 3/2009 | Slepnev et al. |
| 2009/0099335 A1 | 4/2009 | Lacey |
| 2016/0002743 A1 * | 1/2016 | Ray .................. C12Q 1/701 435/5 |
| 2016/0122833 A1 * | 5/2016 | Van Loy ............. C12Q 1/701 506/2 |

FOREIGN PATENT DOCUMENTS

| | | | |
|---|---|---|---|
| EP | 0320308 | 6/1990 | |
| FR | WO 2011023950 A1 * | 3/2011 | ............ C12Q 1/705 |
| IT | WO 2008125366 A2 * | 10/2008 | .......... A61K 31/522 |
| WO | WO 90/01069 | 2/1990 | |
| WO | WO 2010/090757 | 8/2010 | |
| WO | WO 2010/100182 | 9/2010 | |
| WO | WO 2011/085369 | 7/2011 | |
| WO | WO 2011/131192 | 10/2011 | |
| WO | WO 2013/019651 | 2/2013 | |

OTHER PUBLICATIONS

White et al. (Pathogenesis of progressive multifocal leukoencephalopathy—revisited, J Infect Dis. Mar. 1, 2011;203(5):578-86. doi: 10.1093/infdis/jiq097. Epub Jan. 1, 2011).*
White et al. (Pathogenesis of progressive multifocal leukoencephalopathy—revisited, J Infect Dis. Mar. 1, 2011;203(5):578-86. doi: 10.1093/infdis/jig097. Epub Jan. 1, 2011).*
Berger et al. (The manifold faces of PML and the challenge of diagnosis, Neurology. Dec. 6, 2011;77(23):2006-7. doi: 10.1212/WNL.0b013e31823b9c8f. Epub Nov. 9, 2011).*
Ryschkewitscha et al. (Comparison of PCR-southern hybridization and quantitative real-time PCR for the detection of JC and BK viral nucleotide sequences in urine and cerebrospinal fluid, J Virol Methods. Nov. 2004;121(2):217-21).*
Reid et al. (Sequencing and analysis of JC virus DNA from natalizumab-treated PML patients, J Infect Dis. Jul. 15, 2011;204(2):237-44).*
Marshall et al. (Molecular regulation of JC virus tropism: insights into potential therapeutic targets for progressive multifocal leukoencephalopathy, J Neuroimmune Pharmacol. Sep. 2010;5(3):404-17. Epub Apr. 17, 2010).*
White et al. (Pathogenesis of progressive multifocal leukoencephalopathy—revisited, J Infect Dis. Mar. 1, 2011;203(5):578-86. Epub Jan. 12, 2011).*
Gosert et al. (Rearranged JC virus noncoding control regions found in progressive multifocal leukoencephalopathy patient samples increase virus early gene expression and replication rate, J Virol. Oct. 2010;84(20):10448-56. Epub Aug. 4, 2010).*
Newman et al. (Detection of archetype and rearranged variants of JC virus in multiple tissues from a pediatric PML patient, J Med Virol. Jul. 1997;52(3):243-52).*

(Continued)

*Primary Examiner* — Aaron Priest
(74) *Attorney, Agent, or Firm* — Klarquist Sparkman, LLP

(57) ABSTRACT

The disclosure relates to methods and compositions for detecting the presence of Prototype and/or Archetype JC virus in a biological sample from a subject. In some embodiments, the methods include amplifying and detecting a first nucleic acid sequence unique to Archetype JC virus in a biological sample, and a second nucleic acid sequence common to both Archetype and Prototype JC virus in the biological sample. In several embodiments, the methods can be used to identify JC virus in a biological sample from a subject at risk for progressive multifocal leukoencephalopathy. Compositions and kits for use in the disclosed methods are also provided.

19 Claims, 8 Drawing Sheets

(56) References Cited

OTHER PUBLICATIONS

White et al. (hereinafter "White2"; JC virus DNA is present in many human brain samples from patients without progressive multifocal leukoencephalopathy, J Virol. Oct. 1992;66(10):5726-34).*

Agostini, et al. "Rearrangements of archetypal regulatory regions in JC virus genomes from urine." *Research in virology*, vol. 149, No. 3, pp. 163-170 (1998).

Elphick, el al. "The human polyomavirus, JCV, uses serotonin receptors to infect cells." *Science*, vol. 306, No. 5700, pp. 1380-1383 (2004).

Gordon, et al. "The human polyomavirus, JCV, and neurological diseases (review)," *International journal of molecular medicine*, vol. 1, No. 4, pp. 647-702 (1998).

Houff, et al. "Involvement of JC virus-infected mononuclear cells from the bone marrow and spleen in the pathogenesis of progressive multifocal leukoencephalopathy." *The New England journal of medicine*, vol. 318, No. 5, pp. 301-305 (1988).

Segarra-Newnham et al. "Use of cidofovir in progressive multifocal leukoencephalopathy." *Annals of Pharmacotherapy*, vol. 35, No. 6, pp. 741-744 (2001).

Aksamit. "Treatment of non-AIDS progressive multifocal leukoencephalopathy with cytosine arabinoside." *Journal of neurovirology*, vol. 7, No. 4, pp. 386-390 (2001).

Cinque, et al. "The evolving face of human immunodeficiency virus-related progressive multifocal leukoencephalopathy: defining a consensus terminology," *Journal of neuroVirology* vol. 9, No. sl, pp. 88-92 (2003).

Elsner. "Human polyomavirus JC control region variants in persistently infected NS and kidney tissue." *Journal of general virology*, vol. 79, No. 4, pp. 789-799 (1998).

Frisque, et al. "Human polyomavirus JC virus genome." *Journal of Virology*, vol. 51, No. 2, pp. 458-469 (1984).

Funahashi, et al. "Multiplex real-time PCR assay for simultaneous quantification of BK polyomavirus, JC polyomavirus, and adenovirus DNA." *Journal of clinical microbiology*, vol. 48, No. 3, pp. 825-830 (2010).

GenBank Acc. No. AB038249.1, available at: http://www.ncbi.nlm.nih.gov/nuccore/AB038249.1, last accessed Dec. 16, 2014.

GenBank Acc. No. J02226, available at: http://www.ncbi.nlm.nih.gov/nuccore/J02226, last accessed Dec. 16, 2014.

GenBank Acc. No. M35834, available at: http://www.ncbi.nlm.nih.gov/nuccore/M35834, last accessed Dec. 16, 2014.

Grabowski, et al. "Investigation of pre-diagnostic virological markers for progressive multifocal leukoencephalopathy in human immunodeficiency virus-infected patients." *Journal of medical virology*, vol. 81, No. 7, pp. 1140-1150 (2009).

Jensen, et al. "A classification scheme for human polyomavirus JCV variants based on the nucleotide sequence of the noncoding regulatory region." *Journal of neurovirology*, vol. 7, No. 4, 280-287 (2001).

Jensen, et al. "Viral variant nucleotide sequences help expose leukocytic positioning in the JC virus pathway to the CNS," *Journal of leukocyte biology* vol. 65, No. 4, pp. 428-438 (1999).

Katano el al. "A novel real-time PCR system for simultaneous detection of human viruses in clinical samples from patients with uncertain diagnoses." *Journal of medical virology*, vol. 83, No. 2, pp. 322-330 (2011).

Kneitz, et al. "Progressive multifokale Leukoenzephalopathie bei rheumatologischen Erkrankungen," *Zeiischrift für Rheumatologie*, vol. 67, No. 4, pp. 290-294 (2008), (English abstract attached).

MacKenzie, et al. "Association between simian virus 40 DNA and lymphoma in the United Kingdom." , *Journal of the National Cancer Institute*, vol. 95, No. 13, pp. 1001-1003 (2003).

Newman, et al. "Detection of archetype and rearranged variants of JC virus in multiple tissues from a pediatric PML patient." *Journal of medical virology*, vol. 52, No. 3, pp. 243-252 (1997). (Non-English Document with English language Abstract).

Raj, et al. "Transcriptional regulation: lessons from the human neurotropic polyomavirus, JCV." *Virology*, vol. 213, No. 2, pp. 283-291 (1995).

Ryschkewitsch, et al. "Comparison of PCR-southern hybridization and quantitative real-time PCR for the detection of JC and BK viral nucleotide sequences in urine and cerebrospinal fluid." *Journal of virological methods*, vol. 121, No. 2, pp. 217-221 (2004).

Ryschkewitsch, et al. "JC virus persistence following progressive multifocal leukoencephalopathy in multiple sclerosis patients treated with natalizumab." *Annals of neurology*, vol. 68, No. 3, pp. 384-391 (2010).

Ryschkewitsch, et al. "Multiplex qPCR assay for ultra sensitive detection of JCV DNA with simultaneous identification of genotypes that discriminates non-virulent from virulent variants." *Journal of Clinical Virology*, vol. 57, No. 3, pp. 243-248 (2013).

Sweeney, et al. "Cortical and subcortica JC virus infection: two unusual cases of AIDS associated progressive multifocal leukoencephalopathy." *Journal of Neurology, Neurosurgery & Psychiatry*, vol. 57, No. 8, pp. 994-997 (1994).

Tan, et al. "Detection of JC virus DNA and proteins in the bone marrow of HIV-positive and HIV-negative patients: implications for viral latency and neurotropic transformation." *Journal of Infectious Diseases*, vol. 199, No. 6, pp. 881-888 (2009).

Viscidi, et al. "JC virus antibody and viremia as predictors of progressive multifocal leukoencephalopathy in human immunodeficiency virus-1—infected individuals." *Clinical infectious diseases*, vol. 53, No. 7, pp. 711-715 (2011).

White, et al. "Pathogenesis of progressive multifocal leukoencephalopathy—revisited." *Journal of Infectious Diseases*, vol. 203, No. 5, pp. 578-586 (2011).

Yogo, et al. "Isolation of a possible archetypal JC virus DNA sequence from nonimmunocompromised individuals," *Journal of virology*, vol. 64, No. 6, pp. 3139-3143 (1990).

Zambrano, et al. "Detection of human polyomaviruses and papillomaviruses in prostatic tissue reveals the prostate as a habitat for multiple viral infections." *The Prostate*, vol. 53, No. 4, pp. 263-276 (2002).

* cited by examiner

FIG. 1B
Primers and Probes

| | ID | Label | Nucleotide Sequence 5'-3 |
|---|---|---|---|
| Amplifies Archetype Only | JRR-1 | na | GGAGCCCTGGCTGCAT (SEQ ID NO: 3) |
| | JRR-1.1 | VIC | CTGGCAGTTATAGTGAAACC (SEQ ID NO: 5) |
| | JRR-2 | na | TGTGATTAAGGACTATGGGAGG (SEQ ID NO: 4) |
| Amplifies Prototype & Archetype | JCT-3 | na | AGTGTTGGGATCCTGTGTTTTCA (SEQ ID NO: 6) |
| | JCT-1.2 | FAM | CATCACTGGCAAACAT (SEQ ID NO: 8) |
| | JCT-4 | na | GTGGGATGAAGACCTGTTTTGC (SEQ ID NO: 7) |

Nucleotide Numbering System and Position 5'-3'

| | Prototype | Archetype [c] |
|---|---|---|
| JRR-1 | na | 119-134 |
| JRR-1.1 | na | 139-158 |
| JRR-2 | na | 180-159 |
| JCT-3 | 4300-4322 | 4291-4313 |
| JCT-1.2 | 4324-4339 | 4315-4330 |
| JCT-4 | 4370-4349 | 4361-4340 |

FIG. 1C

| Specimens Type | JCV DNA detect total | | | PML Patients with JCV genomes | | | |
|---|---|---|---|---|---|---|---|
| | Total | Specimens | Patients | Totals | P[a] | P/A[b] | A[c] |
| CSF | 222 | 100 | 52 | 52 | 43 | 6 | 3 |
| Plasma | 83 | 41 | 35 | 8 | 7 | 1 | 0 |
| Serum | 36 | 7 | 4 | 2 | 1 | 1 | 0 |
| Urine | 20 | 12 | 6 | 4 | 0 | 2 | 2 |

| Specimens Type | Non-PML Patients with JCV genomes | | | | Copies/ml of JCV genomes detected | | |
|---|---|---|---|---|---|---|---|
| | Totals | P[a] | P/A[b] | A[c] | Range | Average | Median |
| CSF | 0 | 0 | 0 | 0 | 1.0e1–4.3e8 | 3.0e6 | 1.2e2 |
| Plasma | 27 | 17 | 9 | 1 | 1.2e1–1.5e5 | 4.7e3 | 9.7e1 |
| Serum | 2 | 1 | 0 | 1 | 1.3e1–2.7e4 | 4.6e3 | 3.3e1 |
| Urine | 2 | 0 | 0 | 2 | 1.5e1–4.5e8 | 3.9e8 | 3.9e8 |

[a] Potentially pathogenic only.
[b] Both potentially pathogenic and archetype.
[c] Archetype only.

MS-PML

US 9,631,243 B2

METHODS AND COMPOSITIONS FOR IDENTIFYING JC VIRUS

RELATED APPLICATIONS

This is the U.S. National Stage of International Application No. PCT/US2013/046158, filed Jun. 17, 2013, which was published in English under PCT Article 21(2), which in turn claims the benefit of U.S. Provisional Application No. 61/661,289, filed Jun. 18, 2012. The provisional application is incorporated herein in its entirety.

FIELD

This application relates to the field of viral infection, particularly to methods and compositions for identifying JC virus.

BACKGROUND

The human polyomavirus, JC virus, is the etiologic agent of the central nervous system (CNS) demyelinating disease progressive multifocal leukoencephalopathy (PML), a relatively rare disease typically affecting immune compromised patients, though other patients can also be affected. JC virus infection is globally ubiquitous with more than half the population having been exposed. Approximately 30% of exposed individuals will become latently infected in kidney uroepithelial cells, excreting high viral DNA copy numbers into the urine without evidence of any pathologic consequence in any tissues including the brain. Despite the high infection rate, a small minority of healthy subjects with JC virus infection develop PML.

The incidence of PML is highest in HIV-1 infected individuals and is an AIDS defining illness (approximating 3/100 AIDS patients have PML). Further, the incidence of PML is 1/90 in patients with multiple sclerosis (MS) who are treated with more than 24 doses of the monoclonal antibody directed to α4 integrins, natalizumab, and have history of immune suppressive therapy.

Certain JC virus variants are known to have a greater association with PML. For example "Prototype" JC virus is far more pathogenic than "Archetype" JC virus. Known assays to detect the presence of JC virus in a biological sample and distinguish between Archetype and Prototype JC virus are complex, and require a DNA sequencing step to distinguish between Archetype and Prototype JC virus. Thus, there is a need for a simple assay to distinguish JC virus variants (such as Prototype and Archetype variants) in a biological sample, that does not require DNA sequencing, in order to determine if an individual is at increased risk for, or has, PML.

SUMMARY

This disclosure provides a simple, rapid, and useful method for detecting the presence of Archetype and/or Prototype JC virus in a biological sample, which does not require sequencing of JC virus nucleic acid to distinguish between Archetype and Prototype JC virus. Prototype and Archetype JC virus are identified by amplifying and detecting a nucleic acid sequence unique to Archetype JC virus in the biological sample, and a nucleic acid sequence common to both Archetype and Prototype JC virus in the biological sample. Detecting the nucleic acid sequence unique to Archetype JC virus identifies Archetype JC virus in the biological sample. Detecting more of the nucleic acid molecule common to both Archetype and Prototype JC virus than the nucleic acid molecule unique to Archetype JC virus identifies Prototype JC virus in the biological sample. In some embodiments, detecting the absence of the nucleic acid molecule unique to Archetype JC virus and the presence of the nucleic acid molecule common to both Archetype and Prototype JC virus identifies Prototype JC virus in the biological sample.

In some embodiments, the method of detecting the presence of Prototype and/or Archetype JC virus in a biological sample from a subject includes amplifying a first nucleic acid molecule unique to the Archetype virus that may be in the biological sample by using a first oligonucleotide primer pair that includes a forward oligonucleotide primer that includes at least 12 consecutive nucleotides of the nucleotide sequence set forth as nucleotides 93 to 138 of SEQ ID NO: 1 and a reverse oligonucleotide primer that includes at least 12 consecutive nucleotides complementary to nucleotides 159 to 206 of SEQ ID NO: 1. A second nucleic acid molecule that includes a nucleic acid sequence of the JC virus genome present in both Archetype and Prototype JC virus is also amplified from the biological sample. Whether the first and second nucleic acid molecules have been amplified is determined. In several embodiments, determining whether the first and second nucleic acid molecules have been amplified includes determining the amount of the first nucleic acid molecule that has been amplified and the amount of the second nucleic acid molecule that has been amplified. Amplification of the first nucleic acid molecule determines the presence of Archetype JC virus in the biological sample, and amplification of more of the first nucleic acid molecule than the second nucleic acid molecule determines the presence of Prototype JC virus in the biological sample.

Specific primer pairs for the amplifying nucleic acid molecules, and probes for detecting nucleic acid molecules that have been amplified, are also provided. In some embodiments, the forward oligonucleotide primer of the first oligonucleotide pair comprises or consists of the nucleotide sequence set forth as nucleotides 119-134 of SEQ ID NO: 1. In some embodiments, the reverse oligonucleotide primer of the first oligonucleotide pair comprises or consists of the nucleotide sequence complementary to nucleotides 159-180 of SEQ ID NO: 1. In further embodiments, the forward oligonucleotide primer of the first oligonucleotide pair comprises the nucleotide sequence set forth as nucleotides 119-134 of SEQ ID NO: 1, and the reverse oligonucleotide primer of the first oligonucleotide pair comprises the nucleotide sequence complementary to nucleotides 159-180 of SEQ ID NO: 1.

In some embodiments, determining whether the first nucleic acid molecule has been amplified includes the use of a first oligonucleotide probe comprising at least 12 consecutive nucleotides of the nucleotide sequence set forth as nucleotides 115-180 of SEQ ID NO: 1, or the complement thereof. In some embodiments, the first oligonucleotide probe comprises or consists of the nucleotide sequence set forth as nucleotides 139-158 of SEQ ID NO: 1, or the complement thereof.

In some embodiments, the forward oligonucleotide primer of the second oligonucleotide primer pair comprises or consists of the nucleotide sequence set forth as nucleotides 4291-4313 of SEQ ID NO: 1. In additional embodiments, the reverse oligonucleotide primer of the second oligonucleotide primer pair comprises or consists of the nucleotide sequence complementary to nucleotides 4340-4361 of SEQ ID NO: 1. In further embodiments, the forward oligonucleotide primer of the second oligonucleotide primer pair comprises or consists of the nucleotide sequence set forth as nucleotides 4291-4313 of SEQ ID NO: 1, and the reverse oligonucleotide primer of the second oligonucleotide primer pair comprises or consists of the nucleotide sequence complementary to nucleotides 4340-4361 of SEQ ID NO: 1.

In some embodiments, determining whether the second nucleic acid molecule has been amplified comprises the use of a second oligonucleotide probe comprising or consisting of at least 12 consecutive nucleotides of the nucleotide sequence set forth as nucleotides 4313 to 4340 of SEQ ID NO: 1, or the complement thereof. In some embodiments, the second oligonucleotide probe comprises or consists of the nucleotide sequence set forth as nucleotides 4315-4330 of SEQ ID NO: 1, or the complement thereof.

In several embodiments, amplifying the first nucleic acid molecule, amplifying the second nucleic acid molecule, and determining whether the first and second nucleic acid molecules have been amplified includes using a multiplex quantitative real-time polymerase chain reaction (qPCR) assay. In several embodiments, the qPCR assay comprises two or more amplification cycles. In some embodiments, detecting the presence of prototype JC virus in the biological sample includes determining that the second nucleic acid molecule has been amplified in an earlier amplification cycle of the qPCR assay than a cycle in which the first nucleic acid molecule has been amplified.

The biological sample can be, for example, from a subject at risk of developing PML, such as a subject with a weakened immune system, for example, a subject with AIDS or a subject with multiple sclerosis. In several embodiments, the biological sample is a urine, blood, or cerebrospinal fluid (CSF) sample.

In several embodiments, detecting the presence of Prototype JC virus in a biological sample from a subject using the disclosed methods identifies the subject as having an increased risk of developing PML.

Compositions and kits for use with the disclosed methods are also provided.

The foregoing and other features and advantages of this disclosure will become more apparent from the following detailed description of several embodiments which proceeds with reference to the accompanying figures.

BRIEF DESCRIPTION OF THE DRAWINGS

FIG. 1B is set of tables illustrating primers and probes for use with the disclosed multiplex qPCR assay. RR-primers and probe bind nucleotide sequences in the non-coding regulatory-region specific to JC virus Archetype-genome, while JCT-primers and probe bind T-protein coding-sequences conserved in all JC virus genomes. The sequence numbering is according to the Prototype (Mad-1) JC virus genome nucleotide numbering-system (Frisque et al., *J. Virol.*, 51, 458-469, 1984; see JC virus Mad-1 GenBank Acc. No. J02226, incorporated by reference herein as present in Genbank on Nov. 29, 2000) and the Archetype (CY) JC virus regulatory-region nucleotide numbering-system (Yogo et. al., *J. Virol.*, 64, 3139-3143, 1990; see JC virus CY GenBank Acc. No. M35834, incorporated by reference herein as present in Genbank on Apr. 11, 2003).

FIG. 1C is a set of tables illustrating that an embodiment of the discloses multiplex qPCR assay allowed for the determination/identification of JCV genomic that were present in PML and non-PML patients from whom various clinical specimen were available (CSF, plasma, serum, and urine). While no JCV genomes were detected in the CSF of non-PML patients (as expected for a patient clinically defined as "non-PML"), potentially pathogenic (P) variants in the CSF of PML patients were predominant despite the Archetype (P/A, plus A) also being present in some of these CSF specimens. Plasma and serum of PML and non-PML patients demonstrated both potentially pathogenic and the Archetype (P, plus P/A), while only two non-PML patients demonstrated the Archetype alone (A) in blood. Urine of PML patients demonstrated both potentially pathogenic and Archetype (P/A, plus A), while only Archetype (A) was detected in urine of non-PML patients. Ranges of JCV genome copy numbers detected by the multiplex qPCR are also given for each specimen type tested. Despite Archetype being the predominant variant detected in the urines tested, detection of other variants excreted was also shown from these PML patients who have very high copy number of potentially pathogenic variants circulating in their blood and CSF.

FIG. 2A shows the amplification-plot showing the change in fluorescence (Delta Rn) in respect to PCR cycle number (Cycle#) with plasmid concentrations ranging downward from left to right. The threshold (t) is set at a consistent Delta Rn level for all analyses and falls appropriately in the geometric phase for these amplifications. FIG. 2B shows the standard-curve (cycle number read at threshold versus log of the plasmid copy number) for both primer-sets and probes (RR, grey line and shaded-diamond data points; large-T, black line and unshaded-square data points) with plasmid concentrations ranging upward from left to right. This amplification-plot and standard-curve represent a set of quadruplicate reactions run together on a single plate. These data are representative of numerous replicate assays. FIG. 2C shows amplification-plots of multiplex qPCR using the Archetype specific JC virus regulatory region primer-set and probe (JRR-1, JRR-2, JRR-1.1-VIC; grey), in addition to the non-specific JC virus large-T antigen primer-set and probe (JCT-3, JCT-4, JCT-1.2-FAM; black) and eight different concentrations (100 pg, 10 pg, 1 pg, 100 fg, 10 fg, 1 fg, 100 ag, 10 ag) of Prototype JC virus plasmid (pM1TC), each spiked with one concentration (10 fg) of Archetype JC virus plasmid (pCY). FIG. 2D shows corresponding assays with eight different concentrations (100 pg, 10 pg, 1 pg, 100 fg, 10 fg, 1 fg, 100 ag, 10 ag) of Archetype JC virus plasmid (pCY), each spiked with one concentration (10 fg) of Prototype JC virus plasmid (pM1TC). The 10 fg spikes in all amplifications result in the lower concentration (10 fg, 1 fg, 100 ag, 10 ag) large-T antigen plots (black) crossing the threshold (t) in the same general area. The thresholds (t) are set at a consistent Delta Rn level and fall appropriately in the geometric phase for these amplifications. Both amplification-plots represent a set of quadruplicate reactions that were grouped and run together on a single plate.

SEQUENCE LISTING

Figure 1A:
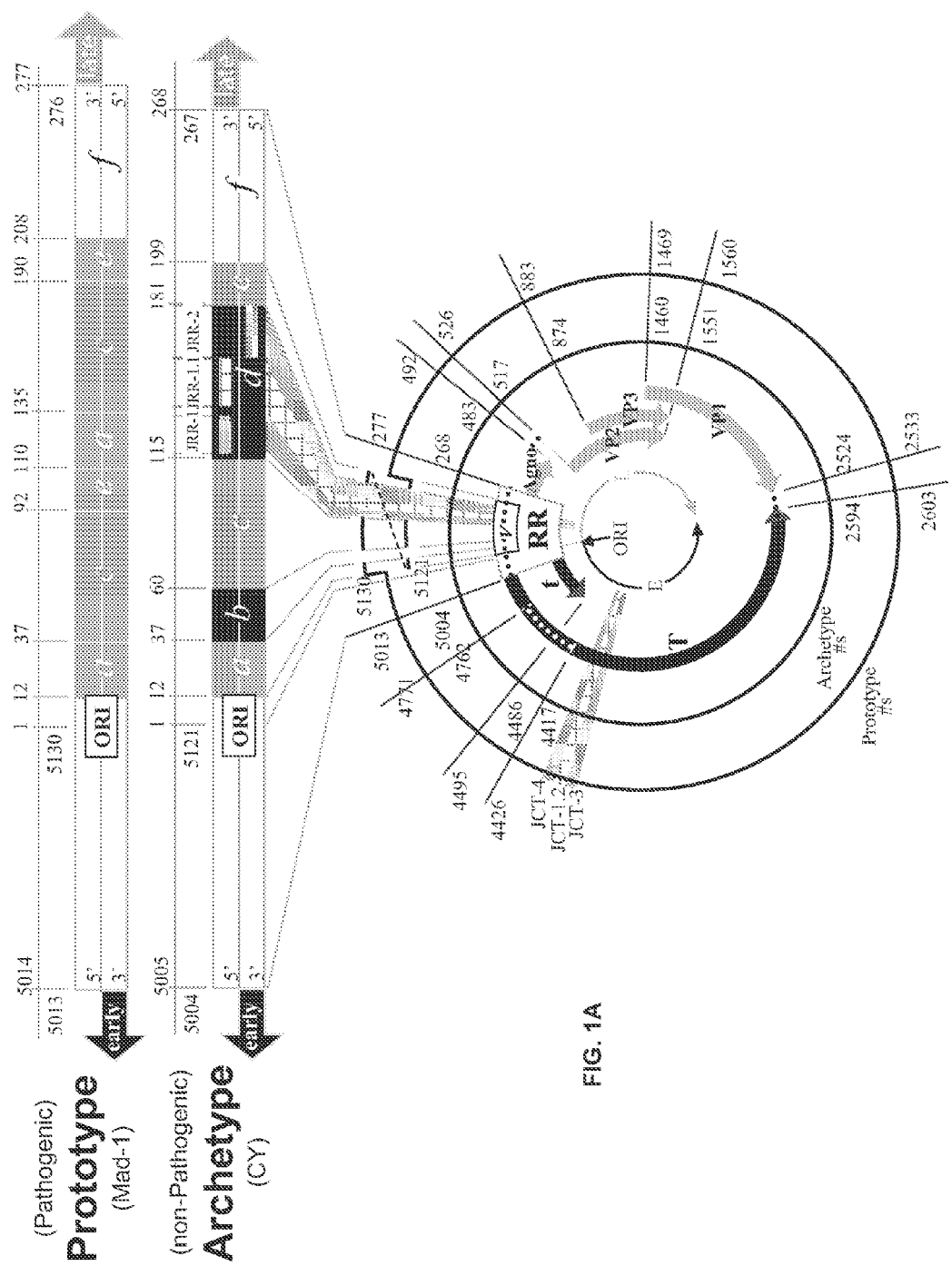
FIG. 1A is a schematic diagram illustrating the comparison between the Prototype (Mad-1 isotype) and Archetype (CY isotype) JC virus genomes, including the location of primer-sets and probes for use in multiplex qPCR analyses described herein. JC virus genomes are circular, supercoiled, double-stranded DNA with an early (E) protein coding region (encoding large-T and small-t antigens) transcribed in one direction from a single strand, and a separate late (L) protein coding region (encoding agnoprotein, Vp1, Vp2 and Vp3) transcribed in the opposite direction from the complementary strand. Between start-sites for the early and late coding regions, and including the origin of DNA replication (ORI), is the non-coding regulatory region (RR in FIG. 1; also termed NCRR herein). Dots on the depicted circular genome represent non-coding nucleotide sequences, including the RR, other intergenic regions, and the spliced portion of large-T message. The RR contains a hypervariable region (v) which can be used to distinguish Archetype and Prototype JC virus genomes. JC virus variants differ in levels of viral activity according to the unique nucleotide sequence of the v region. While Archetype JC virus is considered non-pathogenic, the Prototype JC virus has increased pathogenic activity. The highlighted linear RR comparison between Mad-1 and CY utilizes nucleotide-numbering systems adapted from the Prototype JC virus genome and the Archetype JC virus RR respectively. The Archetype RR contains a single copy of the nucleotide sequence sections observed in the RR of all other JC virus variants. These nucleotide sequence sections are designated a, b, c, d, e and f (see Table 1, below). The unique arrangement, repetition, and/or deletion of the sequence sections in the v region can be used to discriminate between Archetype and Prototype JC virus strains.
Figure 2A:
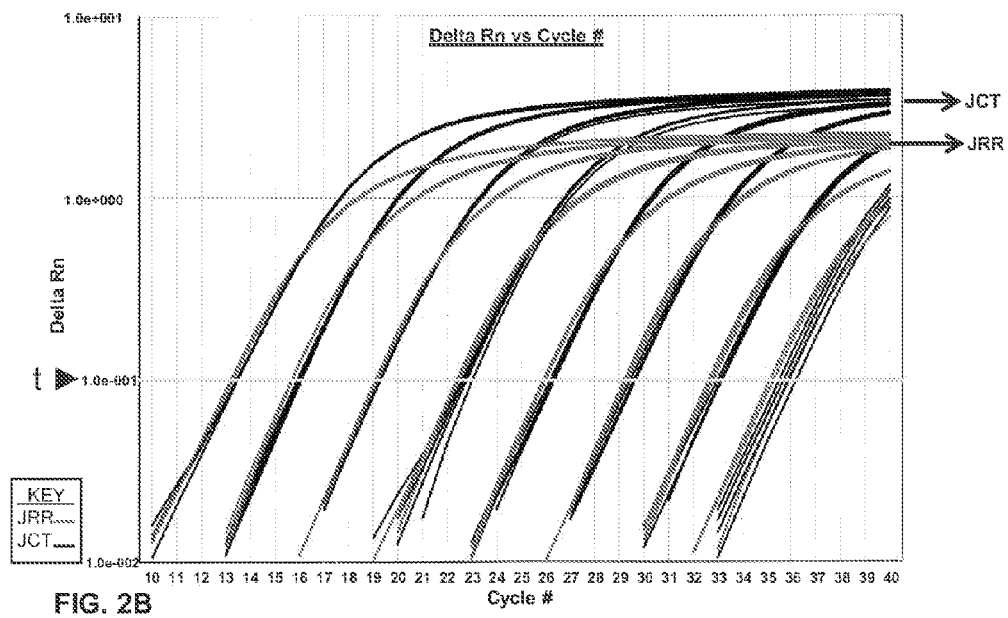
FIGS. 2A-2D are a set of graphs illustrating the multiplex qPCR assay using the JC virus regulatory region (RR) primer-set and probe JRR-1, JRR-2, JRR-1.1-VIC (grey; Archetype specific; "JRR"), in addition to the JC virus large-T antigen primer-set and probe JCT-3, JCT-4, JCT-1.2-FAM (black; non-specific; "JCT"), and eight different concentrations (100 picograms (pg), 10 pg, 1 pg, 100 femptograms (fg), 10 fg, 1 fg, 100 attograms (ag), 10 ag) of Archetype JC virus plasmid (pCY).
Figure 2B:
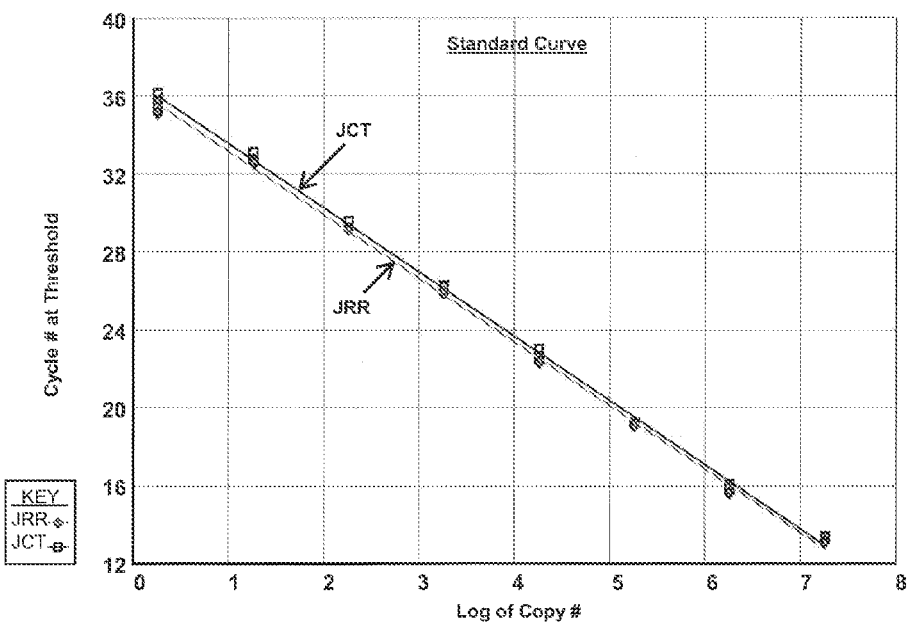
Figure 2C:
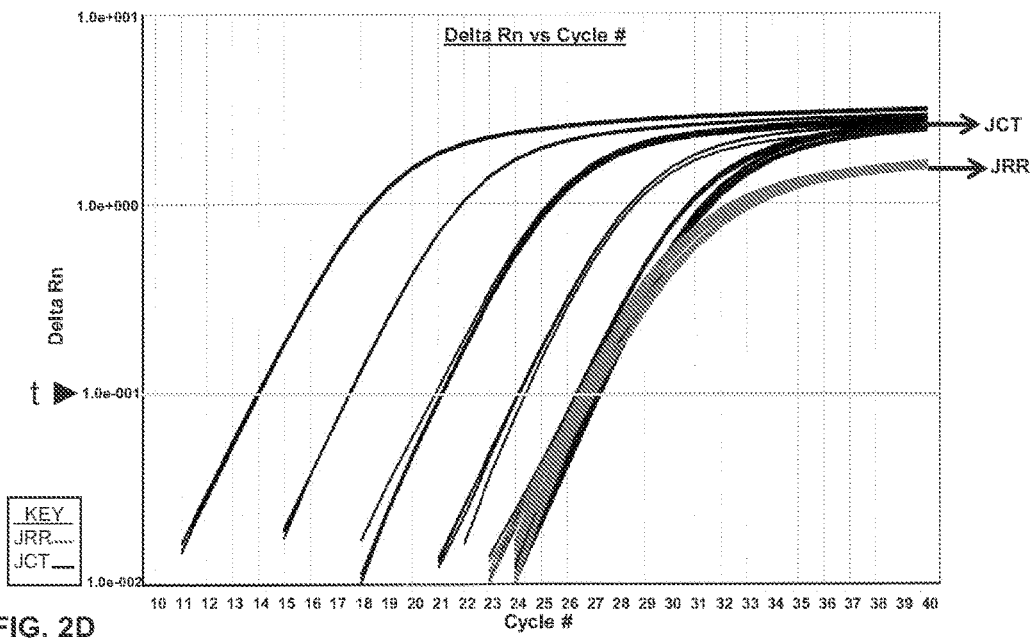
Figure 2D:
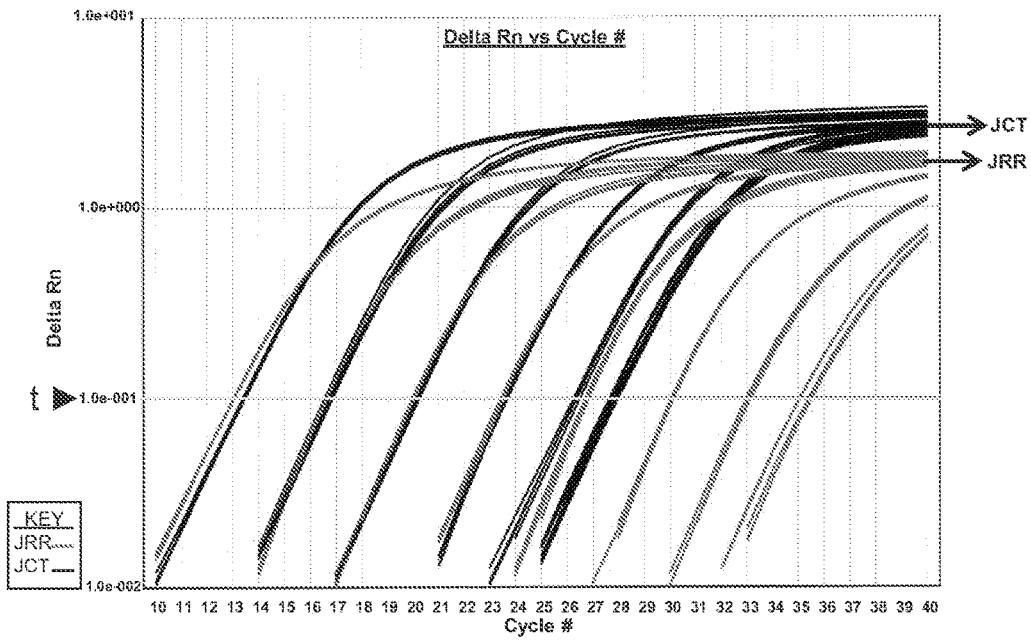

The nucleic and amino acid sequences provided herein are shown using standard letter abbreviations for nucleotide bases, and three letter code for amino acids, as defined in 37 C.F.R. 1.822. Only one strand of each nucleic acid sequence is shown.

The Sequence Listing is submitted as an Annex C/St.25 text file, named "Sequence.txt," created on Nov. 8, 2016, ~16 kb, which is incorporated by reference herein. In the accompanying sequence listing:

SEQ ID NO: 1 is the nucleotide sequence of Archetype JC Polyomavirus DNA, complete genome, Isolate CY (Genbank Accession No. AB038249.1, incorporated by reference herein as present in Genbank on Nov. 8, 2007). Nucleotides 1-270 of SEQ ID NO:1 are the Archetype Regulatory Region (Genbank Accession No. M35834, incorporated by reference herein as present in Genbank on Apr. 11, 2003).

SEQ ID NO: 2 is the nucleotide sequence of Prototype JC Polyomavirus DNA, complete genome, Isolate Mad-1 (Genbank Accession No. Accession No. J02226, incorporated by reference herein as present in Genbank on Nov. 29, 2000).

DETAILED DESCRIPTION

The genotype of JC virus excreted in the urine of healthy subjects, considered non-pathogenic, has a unique arrangement of non-coding regulatory region (NCRR) nucleotide sequences. Viral variants with this nucleotide structure, termed 'Archetype,' have rarely been associated with PML. However, select deletions and duplications in the Archetype NCRR that result in direct tandem repeats can give rise to the arrangement of the pathogenic variant, termed "Prototype" (Jensen and Major, *J Neurovirol.*, 7:280-7, 2001). Prototype JC virus can be found in numerous tissues, including urine, blood (e.g., serum), brain tissue, and cerebrospinal fluid (CSF). Although Prototype viremia present in tissues is not a general diagnostic aid for PML, since it can be found in approximately 2% of the general population, it can be a considerable risk factor in patients with underlying immune compromised conditions (Viscidi, et al., *Clin. Inf. Diseases*, 53: 711-715, 2011).

Consequently, the identification of JC virus genotype as pathogenic (Prototype) or non-pathogenic (Archetype) provides value in determining which subjects (such as subjects with a compromised immune system) may be at greater risk for developing PML. However, the currently available qPCR assays (including multiplex qPCR assays) can distinguish JC virus from other DNA viruses but cannot distinguish between JC virus types (such as Archetype and Prototype) (Jensen and Major, *J. Leukoc. Biol.*, 65:428-38, 1999). Thus, DNA sequencing is currently required to distinguish between JC virus variants.

This disclosure provides novel assays for detecting the presence of Archetype and/or Prototype JC virus in a biological sample. Prototype and Archetype JC virus are identified by detecting the presence or absence of the unique Archetype nucleic acid sequence in the NCRR of JC virus in a biological sample, and the presence or absence of a nucleic acid sequence common to both Archetype and Prototype JC virus in the biological sample. While the sequences of Archetype and Prototype JC virus are known, these are the first assays that allow discrimination between Prototype and Archetype JV virus in a simple assay, without the need for DNA sequencing. The identification of a JC virus as Prototype can lead to early treatment of infected individuals, and can be used to select therapeutic agents for a subject.

I. Terms

Unless otherwise noted, technical terms are used according to conventional usage. Definitions of common terms in molecular biology may be found in Benjamin Lewin, *Genes*

X, published by Jones & Bartlett Publishers, 2009; and Meyers et al. (eds.), *The Encyclopedia of Cell Biology and Molecular Medicine*, published by Wiley-VCH in 16 volumes, 2008. As used herein, the term "comprises" means "includes." It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting.

To facilitate review of the various embodiments, the following explanations of terms are provided:

3' end: The end of a nucleic acid molecule that does not have a nucleotide bound to it 3' of the terminal residue.

5' end: The end of a nucleic acid sequence where the 5' position of the terminal residue is not bound by a nucleotide.

Administration: To provide or give a subject an agent, for example, a composition that includes an anti-PML agent or anti-viral agent by any effective route. Exemplary routes of administration include, but are not limited to, oral, injection (such as subcutaneous, intramuscular, intradermal, intraperitoneal, and intravenous), sublingual, transdermal (e.g., topical), intranasal and inhalation routes.

Agent: Any substance or any combination of substances that is useful for achieving an end or result; for example, a substance or combination of substances useful for decreasing or reducing PML in a subject. Agents effector molecules and detectable markers. The skilled artisan will understand that particular agents may be useful to achieve more than one result.

Amplification: A technique that increases the number of copies of a nucleic acid molecule (such as an RNA or DNA). An example of amplification is polymerase chain reaction (PCR), in which a sample is contacted with a pair of oligonucleotide primers under conditions that allow for the hybridization of the primers to a nucleic acid template in the sample. The primers are extended under suitable conditions, dissociated from the template, re-annealed, extended, and dissociated to amplify the number of copies of the nucleic acid. The product of amplification can be characterized by electrophoresis, restriction endonuclease cleavage patterns, oligonucleotide hybridization or ligation, and/or nucleic acid sequencing using standard techniques.

Other examples of amplification include quantitative real-time polymerase chain reaction (qPCR), strand displacement amplification, as disclosed in U.S. Pat. No. 5,744,311; transcription-free isothermal amplification, as disclosed in U.S. Pat. No. 6,033,881; repair chain reaction amplification, as disclosed in PCT publication WO 90/01069; ligase chain reaction amplification, as disclosed in European patent publication EP-A-320,308; gap filling ligase chain reaction amplification, as disclosed in U.S. Pat. No. 5,427,930; and NASBA RNA transcription-free amplification, as disclosed in U.S. Pat. No. 6,025,134. Several embodiments include multiplex qPCR assays, which are useful for amplifying and detecting multiple nucleic acid sequences (such as the d section of the hypervariable region of the JC virus NCRR and a nucleotide sequence present in both Archetype and Prototype JC virus) in a single reaction.

Anti-PML agent: A molecule that inhibits PML in a subject. Exemplary anti-PML agents include cytosine arabinoside (ARA C) (see, for example, Aksamit, J Neurovirol., 7:386-390, 2001) cidofovir (see, for example, Segarra-Newnham and Vodolo, Ann Pharmacther, 35:741-744, 2001), and inhibitors of 5HT2A serotonin receptor (Elphick G. F. Science 306: 1380-1383, 2004.

Autoimmune disorder: A disease in which the immune system produces an immune response (e.g., a B cell or a T cell response) against an antigen that is part of the normal host, with consequent injury to tissue. An exemplary autoimmune disorder is multiple sclerosis. Additional autoimmune disorders are known to the person of ordinary skill in the art, and further described herein.

Biological sample: A sample of biological material obtained from a subject. Biological samples include all clinical samples useful for detection of disease or infection (e.g., JC virus infection) in subjects. Appropriate samples include any conventional biological samples, including clinical samples obtained from a human or veterinary subject. Exemplary samples include, without limitation, cells, cell lysates, blood smears, cytocentrifuge preparations, cytology smears, bodily fluids (e.g., blood, plasma, serum, saliva, sputum, urine, bronchoalveolar lavage, semen, cerebrospinal fluid (CSF), etc.), tissue biopsies or autopsies, fine-needle aspirates, and/or tissue sections. In a particular example, a biological sample is obtained from a subject having, suspected of having or at risk of having, PML; for example, a subject having HIV infection, or a subject with multiple sclerosis being treated with natalizumab.

Conservative variant: A "conservative variant" of a probe or primer includes sequences that have altered nucleic acid sequences, but retain their ability to bind to the target sequences (and identify or amplify the target sequence) with sufficient specificity. In some particular examples, no more than about 1, 2, 5, or 10 nucleic acids are changed, or the probe or primer retains at least 80%, 85%, 90%, or 95% sequence identity to the original sequence. Conservative variants also include probe or primer sequences to which additional sequence has been added, while still retaining the noted specificity of the probe or primer.

Consists of or consists essentially of: With regard to a polynucleotide (such as a probe or primer), a polynucleotide consists essentially of a specified nucleotide sequence if it does not include any additional nucleotides. However, the polynucleotide can include additional non-nucleic acid components, such as labels (for example, fluorescent, radioactive, or solid particle labels), sugars or lipids. With regard to a polynucleotide, a polynucleotide that consists of a specified nucleotide sequence does not include any additional nucleotides, nor does it include additional non-nucleic acid components, such as lipids, sugars or labels.

Contacting: Placement in direct physical association, for example solid, liquid or gaseous forms. Contacting includes, for example, direct physical association of fully- and partially-solvated molecules.

Control: A sample or standard used for comparison with an experimental sample. In some embodiments, the control is a sample obtained from a healthy patient or a non-PML tissue sample obtained from a patient at risk of PML, or a sample from a subject with PML. In some embodiments, the control is a sample including Archetype or Prototype JC virus nucleic acid. In other embodiments, the control is a biological sample obtained from a patient diagnosed with PML. In still other embodiments, the control is a historical control or standard reference value or range of values (such as a previously tested control sample, such as a group of JC virus patients with known prognosis or outcome, or group of samples that represent baseline or normal values, such as the presence or absence of Prototype or Archetype JC virus in a biological sample.

Detecting: To identify the existence, presence, or fact of something. General methods of detecting are known to the skilled artisan and may be supplemented with the protocols and reagents disclosed herein. For example, included herein are methods of detecting a Prototype JC virus in a biological sample. In some examples, detecting a Prototype JC virus in a biological sample detects PML in the subject from whom the biological sample was obtained. Detection can include a physical readout, such as fluorescence or a reaction output.

Detectable marker: A detectable molecule (also known as a label) that is conjugated directly or indirectly to a second molecule, such as a nucleic acid molecule, to facilitate detection of the second molecule. The person of ordinary skill in the art is familiar with detectable markers for labeling nucleic acid molecules and their use. For example, the detectable marker can be capable of detection by ELISA, spectrophotometry, flow cytometry, or microscopy. Specific, non-limiting examples of detectable markers include fluorophores, fluorescent proteins, chemiluminescent agents, enzymatic linkages, radioactive isotopes and heavy metals or compounds. In several embodiments, the detectable markers are designed for use with qPCR, such as multiplex qPCR. Various methods of labeling nucleic acid molecules are known in the art and may be used.

Diagnosis: The process of identifying a disease by its signs, symptoms and results of various tests. The conclusion reached through that process is also called "a diagnosis." Forms of testing commonly performed include blood tests, medical imaging, urinalysis, and biopsy.

Human Immunodeficiency Virus (HIV): A retrovirus that causes immunosuppression in humans (HIV disease), and leads to a disease complex known as the acquired immunodeficiency syndrome (AIDS). "HIV disease" refers to a well-recognized constellation of signs and symptoms (including the development of opportunistic infections) in persons who are infected by an HIV virus, as determined by antibody or western blot studies. Laboratory findings associated with this disease include a progressive decline in T cells. HIV includes HIV type 1 (HIV-1) and HIV type 2 (HIV-2). Related viruses that are used as animal models include simian immunodeficiency virus (SIV), and feline immunodeficiency virus (FIV). Treatment of HIV-1 with retroviral therapy has been effective in reducing the viral burden and ameliorating the effects of HIV-1 infection in infected individuals.

Hybridization: The terms "annealing" and "hybridization" refer to the formation of base pairs between complementary regions of DNA, RNA, or between DNA and RNA of nucleic acids. Examples of annealing and hybridization include formation of base pairs between two separate nucleic acid molecules, as well as formation of base pairs between nucleic acids on a single nucleic acid molecule.

In some examples, hybridization is between two complementary nucleic acid sequences, for example nucleic acid sequences that are at least 90% complementary to each other, such as at least 91%, 92%, 93%, 94%, 95%, 96%, 97%, 98%, 99%, or 100% complementary to each other.

In additional embodiments, hybridization conditions resulting in particular degrees of stringency and specificity will vary depending upon the nature of the hybridization method and the composition and length of the hybridizing nucleic acid sequences. Generally, the temperature of hybridization and the ionic strength (such as the $Na^+$ concentration) of the hybridization buffer will determine the stringency of hybridization. Calculations regarding hybridization conditions for attaining particular degrees of stringency are discussed in Sambrook et al., (1989) *Molecular Cloning*, second edition, Cold Spring Harbor Laboratory, Plainview, N.Y. (chapters 9 and 11). The following is an exemplary set of hybridization conditions and is not limiting:

Very High Stringency (Detects Sequences that Share at Least 90% Identity)
Hybridization: 5×SSC at 65° C. for 16 hours
Wash twice: 2×SSC at room temperature (RT) for 15 minutes each
Wash twice: 0.5×SSC at 65° C. for 20 minutes each
High Stringency (Detects Sequences that Share at Least 80% Identity)
Hybridization: 5×-6×SSC at 65° C.-70° C. for 16-20 hours
Wash twice: 2×SSC at RT for 5-20 minutes each
Wash twice: 1×SSC at 55° C.-70° C. for 30 minutes each
Low Stringency (Detects Sequences that Share at Least 50% Identity)
Hybridization: 6×SSC at RT to 55° C. for 16-20 hours
Wash at least twice: 2×-3×SSC at RT to 55° C. for 20-30 minutes each.

In some embodiments, the probes and primers disclosed herein can hybridize to nucleic acid molecules under low stringency, high stringency, and very high stringency conditions.

Immunosuppressive agent: A molecule, such as a chemical compound, small molecule, steroid, nucleic acid molecule, protein (such as an antibody) or other biological agent, that can decrease an immune response such as an inflammatory reaction. Immunosuppressive agents include, but are not limited to, agents of use in treating multiple sclerosis. Specific, non-limiting examples of immunosuppressive agents are natalizumab (Biogen Idec, Weston, Mass.), rituximab (Genetech, South San Francisco, Calif.), efalizumab (Genetech, South San Francisco, Calif.), brentuximab vedotin (Seattle Genetics, Seattle Wash.), fingolimod (Novartis AG, Basal, CH), mycophenolate mofetil (Genetech, South San Francisco, Calif.).

Inhibiting or treating a disease: Inhibiting the full development of a disease or condition, for example, in a subject who is at risk for a disease such as PML. "Treatment" refers to a therapeutic intervention that ameliorates a sign or symptom of a disease or pathological condition after it has begun to develop. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in viral titer, an improvement in the overall health or well-being of the subject, or by other parameters well known in the art that are specific to the particular disease. A "prophylactic" treatment is a treatment administered to a subject who does not exhibit signs of a disease or exhibits only early signs for the purpose of decreasing the risk of developing pathology.

Isolated: An "isolated" biological component (such as a nucleic acid molecule or protein) has been substantially separated or purified away from other biological components in the cell of the organism in which the component naturally occurs. The term "isolated" does not require absolute purity. Nucleic acids and proteins that have been "isolated" include nucleic acids and proteins purified by standard purification methods. The term also embraces nucleic acids and proteins prepared by recombinant expression in a host cell, as well as chemically synthesized nucleic acids.

JC virus (JCV): A small DNA virus of the polyomavirus family. JC virus is the etiologic agent of the CNS demyelinating disease progressive multifocal leukoencephalopathy (PML), a relatively rare disease typically affecting immune compromised patients. JC virus infection is globally ubiquitous and approximately 30% of exposed individuals will become latently infected in kidney uroepithelial cells, excreting high viral DNA copy numbers into the urine without evidence of any pathologic consequence in any tissues including the brain (Grabowski et al., *J. Med. Virol.*, 81: 1140-1150, 2009).

The JC virus genome can be divided into three regions that encompass the transcription control region; the genes responsible for the expression of the viral early protein, T antigen; and the genes encoding the viral late proteins, VP1, VP2, and VP3. Within the transcription control region is the non-coding regulatory region (NCRR) nucleotide sequences. The genotype of urine excreted virus in healthy subject (e.g., those without PML), considered non-pathogenic, has a unique arrangement of nucleotides of a hypervariable region within the NCRR. The unique arrangement includes six different nucleotide sequences, termed sections: a, b, c, d, e and f, following the nomenclature adopted by Elsner and Dorries in "Human polyomavirus JC control region variants in persistently infected CNS and kidney tissue," J. Gen. Virol., 79:789-799, 1998. Viral variants with this nucleotide structure, termed the "Archetype," are rarely associated with PML. However, viral variants that lack the "d" section of the hypervariable region of the NCRR can give rise to the arrangement of the pathogenic virus associated with PML, termed "Prototype" (Jensen and Major, *J Neurovirol.*, 7:280-7, 2001). As used herein, "Archetype" JC virus refers to JC virus with a genome containing the "d" section of the hypervariable region of the NCRR in its entirety (corresponding to nucleotides 115-180 of SEQ ID NO: 1), and "Prototype" JC virus refers to JC virus that lacks the "d" section of the hypervariable region of the NCRR or may contain partial sequences (such as no more than 1, 2, 3, 4, 5, 6, 7, 8, 9, or no more than 10 nucleotides of the "d" section of the hypervariable region of the NCRR, corresponding to nucleotides 115-180 of SEQ ID NO: 1). Other regions of the Archetype and Prototype JC virus genome (such as the T protein coding region) can maintain similar nucleic acid sequences.

Nucleic acid sequences for the genome of Archetype and Prototype JC virus are known. An exemplary nucleic acid sequence for Archetype JC virus is provided as SEQ ID NO: 1 (JC virus isolate CY; Genbank Accession No. AB038249.1, incorporated by reference herein as present in Genbank on Nov. 9, 2007). An exemplary nucleic acid sequence for Prototype JC virus is provided as SEQ ID NO: 2 (JC virus isolate Mad-1; Genbank Accession No. Accession No. J02226, incorporated by reference herein as present in Genbank on Nov. 30, 2009). The nucleic acid sequences of the hypervariable regions corresponding to these exemplary Archetype and Prototype JC virus sequences are provided in Tables 1 and 2, below.

Multiple sclerosis: An autoimmune disease classically described as a central nervous system white matter disorder disseminated in time and space that presents as relapsing-remitting illness in 80-85% of patients. Diagnosis can be made by brain and spinal cord magnetic resonance imaging (MRI), analysis of somatosensory evoked potentials, and analysis of cerebrospinal fluid to detect increased amounts of immunoglobulin or oligoclonal bands. Several treatments for multiple sclerosis are known, including treatment with interferon-$\beta$ (IFN-$\beta$) as well as treatment with the monoclonal antibodies alemtuzumab, daclizumab, rituximab and natalizumab.

Multiplex qPCR: Amplification and detection of multiple nucleic acid species in a single qPCR reaction. By multiplexing, target nucleic acids can be amplified in single tube. In some examples, multiplex PCR permits the simultaneous detection of the amplification products of a region of the JC virus genome specific to Archetype JC virus, and a region of the JC virus genome common to both Archetype and Prototype JC virus using the disclosed probes.

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. It will be understood that when a nucleotide sequence is represented by a DNA sequence (i.e., A, T, G, C), this also includes an RNA sequence (i.e., A, U, G, C) in which "U" replaces "T."

"Nucleotide" includes, but is not limited to, a monomer that includes a base linked to a sugar, such as a pyrimidine, purine or synthetic analogs thereof, or a base linked to an amino acid, as in a peptide nucleic acid (PNA). A nucleotide is one monomer in a polynucleotide. A nucleotide sequence refers to the sequence of bases in a polynucleotide.

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

"cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (for example, rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns. In some examples, a nucleic acid encodes a disclosed antigen.

Oligonucleotide probes and primers: A probe includes an isolated nucleic acid (usually of 100 or fewer nucleotide residues) attached to a detectable label or reporter molecule, which is used to detect a complementary target nucleic acid molecule by hybridization and detection of the label or reporter. Isolated oligonucleotide probes (which as defined herein also include the complementary sequence and corresponding RNA sequences) are of use for detection of JC virus sequences. Typically, probes are at least about 10 nucleotides in length, such as at least about 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or about 100 nucleotides in length. For example, a probe can be about 10-100 nucleotides in length, such as, 12-15, 12-20, 12-25, 12-30, 12-35, 12-40, 12-45, 12-50, 12-80, 14-15, 14-16, 14-18, 14-20, 14-25, 14-30, 15-16, 15-18, 15-20, 15-25, 15-30, 15-35, 15-40, 15-45, 15-50, 15-80, 16-17, 16-18, 16-20, 16-22, 16-25, 16-30, 16-40, 16-50, 17-18, 17-20, 17-22, 17-25, 17-30, 18-19, 18-20, 18-22, 18-25, 18-30, 19-20, 19-22, 19-25, 19-30, 20-21, 20-22, 20-25, 20-30, 20-35, 20-40, 20-45, 20-50, 20-80, 21-22, 21-25, 21-30, 22-25, 22-30, 22-40, 22-50, 23-24, 23-25, 23-30, 24-25, 24-30, 25-35, 25-30, 25-35, 25-40, 25-45, 25-50 or 25-80 nucleotides in length.

Primers are nucleic acid molecules, usually DNA oligonucleotides of about 10-50 nucleotides in length (longer lengths are also possible). Typically, primers are at least about 10 nucleotides in length, such as at least about 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or about 50 nucleotides in length. For example, a primer can be about 10-50 nucleotides in length, such as, 12-15, 12-20, 12-25, 12-30, 12-35, 12-40, 12-45, 12-50, 14-15, 14-16, 14-18, 14-20, 14-25, 14-30, 15-16, 15-18, 15-20, 15-25, 15-30, 15-35, 15-40, 15-45, 15-50, 16-17, 16-18, 16-20, 16-22, 16-25, 16-30, 16-40, 16-50, 17-18, 17-20, 17-22, 17-25, 17-30, 18-19, 18-20, 18-22, 18-25, 18-30, 19-20, 19-22, 19-25, 19-30, 20-21, 20-22, 20-25, 20-30, 20-35, 20-40, 20-45, 20-50, 21-22, 21-25, 21-30, 22-25, 22-30, 22-40, 22-50, 23-24, 23-25, 23-30, 24-25, 24-30, 25-30, 25-35, 25-40 or 25-45, 25-50 nucleotides in length.

Probes and primers can also be of a maximum length, for example no more than 15, 25, 25, 40, 50, 75 or 100 nucleotides in length.

Primers may be annealed to a complementary target DNA strand by nucleic acid hybridization to form a hybrid between the primer and the target DNA strand, and then extended along the target DNA strand by a DNA polymerase enzyme. One of skill in the art will appreciate that the hybridization specificity of a particular probe or primer typically increases with its length. Thus, for example, a probe or primer including 20 consecutive nucleotides typically will anneal to a target with a higher specificity than a corresponding probe or primer of only 15 nucleotides. In some embodiments, probes and primers are used in combination in a qPCR reaction.

Operably linked: A first molecule, such as a nucleic acid or protein, is operably linked with a second molecule when the first molecule is placed in a functional relationship with the second molecule. For instance, a promoter is operably linked to a nucleic acid coding sequence if the promoter affects the transcription or expression of the coding sequence. Additionally, an intron is operably linked to an exon for the function of splicing. Generally, operably linked nucleotide sequences are contiguous.

Primer pair: Two primers (one "forward" and one "reverse") that can be used for amplification of a nucleic acid sequence, for example by polymerase chain reaction (PCR) or other in vitro nucleic-acid amplification methods. The forward and reverse primers of a primer pair do not hybridize to overlapping complementary sequences on the target nucleic acid sequence.

Progressive Multifocal Leukoencephalopathy (PML): A typically fatal or sometimes chronic illness that is a demyelinating disease of the central nervous system which results from replication of Prototype JC virus in macroglial cells of the human brain. PML typically affects subjects with an impaired immune system, such as, but not limited to, a subject with HIV infection.

It has been reported that approximately 3% of AIDS patients exhibit signs of PML, and JC virus has been detected in the cerebrospinal fluid (CSF) of affected patients, suggesting that there is active replication of the virus in the brain. In addition, PML has been seen in patients undergoing treatment with natalizumab, an alpha-4 integrin specific monoclonal antibody.

The typical hallmarks of PML include multifocal demyelinated lesions with enlarged eosinophilic nuclei in oligodendrocytes and enlarged bizarre astrocytes with lobulated hyperchromatic nuclei within white matter tracts of the brain (Cinque, P., (2003). J. Neurovirol. 9 (Suppl. 1):88-92), although in some instances atypical features that include a unifocal pattern of demyelination and involvement of the gray matter have been reported (Sweeney, B. J., (1994). J. Neurol. Neurosurg. Psychiatry 57:994-997). Oligodendrocytes and astrocytes are known to support productive viral infections (Gordon, J. (1998) Int. J. Mol. Med. 1:647-655; Raj, G. V., (1995) Virology 10:283-291).

Quantitative real-time PCR (qPCR): A method for detecting and measuring products generated during each cycle of a PCR, which are proportionate to the amount of template nucleic acid prior to the start of PCR. The information obtained, such as an amplification curve, can be used to determine the presence of a target nucleic acid (such as a JC virus nucleic acid) and/or quantitate the initial amounts of a target nucleic acid sequence. Exemplary procedures for real-time PCR can be found in "Quantitation of DNA/RNA Using Real-Time PCR Detection" published by Perkin Elmer Applied Biosystems (1999); *PCR Protocols* (Academic Press, New York, 1989); *A-Z of Quantitative PCR*, Bustin (ed.), International University Line, La Jolla, Calif., 2004; and *Quantitative Real-Time PCR in Applied Microbiology*, Filion (Ed), Caister Academic Press, 2012.

In some examples, the amount of amplified target nucleic acid (for example a JC virus nucleic acid) is detected using a labeled probe, such as a probe labeled with a fluorophore, for example a TAQMAN® probe. In this example, the increase in fluorescence emission is measured in real-time, during the course of the real-time PCR. This increase in fluorescence emission is directly related to the increase in target nucleic acid amplification. In some examples, the change in fluorescence (Delta Rn; dRn; ΔRn) is calculated using the equation $dRn=Rn^{+}-Rn^{-}$, with $Rn^{+}$ being the fluorescence emission of the product at each time point and $Rn^-$ being the fluorescence emission of the baseline. The dRn values are plotted against cycle number, resulting in amplification plots for each sample. The threshold value ($C_t$) is the PCR cycle number at which the fluorescence emission (dRn) exceeds a chosen threshold, which is typically 10 times the standard deviation of the baseline (this threshold level can, however, be changed if desired).

The threshold cycle is when the system begins to detect the increase in the signal associated with an exponential growth of PCR product during the log-linear phase. This phase provides information about the reaction. The slope of the log-linear phase is a reflection of the amplification efficiency. The efficiency of the reaction can be calculated by the following equation: $E=10^{(-1/slope)}$, for example. The efficiency of the PCR should be 90-100% meaning doubling of the amplicon at each cycle. This corresponds to a slope of −3.1 to −3.6 in the $C_t$ vs. log-template amount standard curve.

Recombinant: A recombinant nucleic acid is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, e.g., by genetic engineering techniques.

Sensitivity and specificity: Statistical measurements of the performance of a binary classification test. Sensitivity measures the proportion of actual positives which are correctly identified (e.g., the percentage of samples that are identified as including nucleic acid from a particular virus). Specificity measures the proportion of negatives which are correctly identified (e.g., the percentage of samples that are identified as not including nucleic acid from a particular virus).

Sequence identity: The similarity between two nucleic acid sequences, is expressed in terms of the similarity between the sequences, otherwise referred to as sequence identity. Sequence identity is frequently measured in terms of percentage identity, similarity, or homology; a higher percentage identity indicates a higher degree of sequence similarity.

The NCBI Basic Local Alignment Search Tool (BLAST), Altschul et al., *J. Mol. Biol.* 215:403-10, 1990, is available from several sources, including the National Center for Biotechnology Information (NCBI, Bethesda, Md.), for use in connection with the sequence analysis programs blastp, blastn, blastx, tblastn and tblastx. It can be accessed through the NCBI website. A description of how to determine sequence identity using this program is also available on the website.

When less than the entire sequence is being compared for sequence identity, homologs will typically possess at least 75% sequence identity over short windows of 10-20 amino acids, and can possess sequence identities of at least 85% or at least 90% or 95% depending on their similarity to the reference sequence. Methods for determining sequence identity over such short windows are described on the NCBI website.

These sequence identity ranges are provided for guidance only; it is entirely possible that strongly significant homologs could be obtained that fall outside of the ranges provided.

An alternative indication that two nucleic acid molecules are closely related is that the two molecules hybridize to each other under stringent conditions. Stringent conditions are sequence-dependent and are different under different environmental parameters. Generally, stringent conditions are selected to be about 5° C. to 20° C. lower than the thermal melting point (Tm) for the specific sequence at a defined ionic strength and pH. The Tm is the temperature (under defined ionic strength and pH) at which 50% of the target sequence hybridizes to a perfectly matched probe. Conditions for nucleic acid hybridization and calculation of stringencies can be found in Sambrook et al.; and Tijssen, *Hybridization With Nucleic Acid Probes, Part I. Theory and Nucleic Acid Preparation*, Laboratory Techniques in Biochemistry and Molecular Biology, Elsevier Science Ltd., 1993.

Signal: A detectable change or impulse in a physical property that provides information. In the context of the disclosed methods, examples include electromagnetic signals such as light, for example light of a particular quantity or wavelength. In certain examples, the signal is the disappearance of a physical event, such as quenching of light.

Subject: Any mammal, such as humans, non-human primates, pigs, sheep, cows, rodents and the like. In two non-limiting examples, a subject is a human subject or a murine subject. Thus, the term "subject" includes both human and veterinary subjects. A immunocompromised subject is a subject with a suppressed immune system, such as a subject with HIV.

Target nucleic acid molecule: A nucleic acid molecule whose detection, quantitation, qualitative detection, or a combination thereof, is intended. The nucleic acid molecule need not be in a purified form. Various other nucleic acid molecules can also be present with the target nucleic acid molecule. For example, the target nucleic acid molecule can be a specific nucleic acid molecule (which can include RNA or DNA), the amplification of which is intended. In some examples, a target nucleic acid includes a region of the JC virus genome specific to Archetype JC virus, or a region of the JC virus genome common to both Archetype and Prototype JC virus. Purification or isolation of the target nucleic acid molecule, if needed, can be conducted by methods known to those in the art, such as by using a commercially available purification kit or the like.

Therapeutically effective amount: The amount of an agent (such as an anti-PML agent) that alone, or together with one or more additional agents, induces the desired response, such as, for example treatment of PML in a subject. Ideally, a therapeutically effective amount provides a therapeutic effect without causing a substantial cytotoxic effect in the subject.

Several preparations disclosed herein are administered in therapeutically effective amounts. A therapeutically effective amount of an anti-PML agent (or a composition including an anti-PML agent) that is administered to a human or veterinary subject will vary depending upon a number of factors associated with that subject, for example the overall health of the subject. A therapeutically effective amount of the agents can be determined by varying the dosage and measuring the resulting therapeutic response, such as the reduction of symptoms associated with PML. The disclosed agents can be administered in a single dose, or in several doses, as needed to obtain the desired response. However, the therapeutically effective amount of can be dependent on the source applied, the subject being treated, the severity and type of the condition being treated, and the manner of administration.

Under conditions sufficient for: A phrase that is used to describe any environment that permits a desired activity. In one example the desired activity is amplification of a nucleic acid molecule.

II. Exemplary JC Virus Sequences

Several embodiments include amplifying a nucleic acid molecule including a JC virus sequence. Nucleic acid sequences for the genome of Archetype and Prototype JC viruses are known. An exemplary nucleic acid sequence for Archetype JC virus is provided as SEQ ID NO: 1 (JC virus isolate CY; Genbank Accession No. AB038249.1, incorporated by reference herein as present in Genbank on Nov. 8, 2007). An exemplary nucleic acid sequence for Prototype JC virus is provided as SEQ ID NO: 2 (JC virus isolate Mad-1; Genbank Accession No. Accession No. J02226, incorporated by reference herein as present in Genbank on Nov. 29, 2000). Methods and reagents for amplifying JC virus sequences are known in the art (see, e.g., MacKenzie et al., J. Natl Cancer Inst., 95:1001-1003, 2003, Ryschkewitsch et al., *J Virol Methods*. 121:217-221, 2004, and Int. Pub. Nos. WO2013019651 and WO2011131192, each of which is incorporated by reference herein in its entirety. However, known methods do not provide the simplicity and/or specificity of the disclosed methods for detecting Archetype and/or Prototype JC virus in a biological sample.

The JC virus genome can be divided into three regions that encompass the transcription control region; the genes responsible for the expression of the viral early protein, T antigen and small t; and the genes encoding the viral late proteins, agno, VP1, VP2, and VP3. Within the transcription control region is the non-coding regulatory region nucleotide sequences (NCRR), which includes a hypervariable region having a series of nucleic acid sequence "sections" termed a, b, c, d, e and f following the nomenclature adopted by Elsner and Dorries in "Human polyomavirus JC control region variants in persistently infected CNS and kidney tissue," *J. Gen. Virol.*, 79:789-799, 1998. The nucleic acid sequence of the hypervariable region of an exemplary Archetype JC virus is shown in Table 1, including the nucleic acid sequence and location within SEQ ID NO: 1 of sections a, b, c, d, e, and f. Prototype JC virus does not include a section d. The nucleic acid sequence of the hypervariable region of an exemplary Prototype JC virus is shown in Table 2, including the nucleic acid sequence and location within SEQ ID NO: 2 of the sections a, c, e, a, c, e and f.

TABLE 1

Sequence and positioning of Archetype JC virus hypervariable region sections

| JV variety | NCRR section | SEQ ID NO: 1 position | Sequence |
|---|---|---|---|
| Arch. | a | 12-36 | CTGTATATATAAAAAAAGGGAAGG (SEQ ID NO: 9) |
| | b | 37-59 | TAGGGAGGAGCTGGCTAAAACTG (SEQ ID NO: 10) |
| | c | 60-114 | GATGGCTGCCAGCCAAGCATGAGCT CATACCTAGGGAGCCAACCAGCTGA CAGCC (SEQ ID NO: 11) |
| | d | 115-180 | AGAGGGAGCCCTGGCTGCATGCCAC TGGCAGTTATAGTGAAACCCCTCCC ATAGTCCTTAATCACA (SEQ ID NO: 12) |
| | e | 181-198 | AGTAAACAAAGCACAAGG (SEQ ID NO: 13) |

TABLE 1-continued

Sequence and positioning of Archetype JC virus hypervariable region sections

| JV variety | NCRR section | SEQ ID NO: 1 position | Sequence |
|---|---|---|---|
| | f | 199-267 | GGAAGTGGAAAGCAGCCAGGGGAAC ATGTTTTGCGAGCCAGAGCTGTTTT GGCTTGTCACCAGCTGGCC (SEQ ID NO: 14) |

TABLE 2

Sequence and positioning of Prototype JC virus hypervariable region sections

| JV variety | NCRR section | SEQ ID NO: 2 Position | Sequence |
|---|---|---|---|
| Proto. | a | 12-36 | CTGTATATATAAAAAAAGGGAAGG (SEQ ID NO: 9) |
| | c | 37-91 | GATGGCTGCCAGCCAAGCATGAGCT CATACCTAGGGAGCCAACCAGCTAA CAGCC (SEQ ID NO: 15) |
| | e | 92-109 | AGTAAACAAAGCACAAGG (SEQ ID NO: 13) |
| | a | 110-134 | CTGTATATATAAAAAAAGGGAAGG (SEQ ID NO: 9) |
| | c | 135-189 | GATGGCTGCCAGCCAAGCATGAGCT CATACCTAGGGAGCCAACCAGCTAA CAGCC (SEQ ID NO: 15) |
| | e | 190-207 | AGTAAACAAAGCACAAGGGGAAGTG GAAAGCAGCCAAGG (SEQ ID NO: 16) |
| | f | 208-276 | GAACATGTTTTGCGAGCCAGAGCTG TTTTGGCTTGTCACCAGCTGGCC (SEQ ID NO: 17) |

III. Detecting Archetype and Prototype JC Virus

Methods of detecting the presence of Prototype and/or Archetype JC virus in a biological sample are provided herein. Several embodiments include amplification from a biological sample of a first nucleic acid molecule and detecting the presence or absence of the first amplified nucleic acid molecule, wherein the first nucleic acid molecule include nucleotides from the d section of the hypervariable region of the Archetype JC virus genome (such as at least 30 consecutive nucleotides of the d section of the hypervariable region of the Archetype JC virus genome, for example, at least 35, 40, 45, 50, 55, 60 or 65 consecutive nucleotides). The methods further include amplifying a second nucleic acid molecule from the biological sample including a nucleic acid sequence of the JC virus genome present in both Archetype and Prototype JC virus and detecting the presence or absence of the second amplified nucleic acid molecule. Detection of the presence of the first amplified nucleic acid molecule and the presence of the second amplified nucleic acid molecule detects the presence of Archetype JC virus in the biological sample, and detection of the absence of the first amplified nucleic acid molecule and the presence of the second amplified nucleic acid molecule detects the presence of Prototype JC virus in the biological sample.

In some embodiments, the methods include amplifying from a biological sample a first nucleic acid molecule and detecting the first amplified nucleic acid molecule, wherein the first nucleic acid molecules include nucleotides from the d section of the hypervariable region of the Archetype JC virus genome (such as at least 30 consecutive nucleotides of the d section of the hypervariable region of the Archetype JC virus genome, for example, at least 35, 40, 45, 50, 55, 60 or 65 consecutive nucleotides). The methods further include amplifying a second nucleic acid molecule from the biological sample including a nucleic acid sequence of the JC virus genome present in both Archetype and Prototype JC virus and detecting the second amplified nucleic acid molecule. Detection of the first amplified nucleic acid molecule identifies Archetype JC virus in the biological sample, and detecting more of the first amplified nucleic acid molecule than the second amplified nucleic acid molecule identifies Prototype JC virus in the biological sample. In some embodiments, detecting more of the first amplified nucleic acid molecule than the second amplified nucleic acid molecule includes detecting the absence of the first amplified nucleic acid molecule and the presence of the second amplified nucleic acid molecule.

Methods for amplifying nucleic acid molecules (e.g., using oligonucleotide primer pairs) are familiar to the person of ordinary skill in the art, and further described herein. In several embodiments, nucleic acid molecules are amplified using qPCR (such as multiplex qPCR).

The disclosed methods of amplifying and detecting JC virus sequences can be used to identify the Archetype and/or Prototype JC virus in the biological sample (such as the presence or absence of Archetype and/or Prototype JC virus in the biological sample). For example, the d section (nucleotides 115-180 of SEQ ID NO: 1) of the hypervariable region of the NCRR Archetype JC virus is not present in the hypervariable region of the NCRR of Prototype JC virus. Thus, detecting the presence of the "d" section in a nucleic acid molecule amplified from the biological sample identifies the presence of Archetype JC virus in the biological sample. It will be understood that some JC viral strains include a few nucleotides of the "d" section of the hypervariable region of the NCRR Archetype JC virus (such as no more than 1, 2, 3, 4, or no more than 5 nucleotides of the "d" section of the hypervariable region of the NCRR, corresponding to nucleotides 115-180 of SEQ ID NO: 1) and are still considered to be prototype JC viral strains. In several embodiments, the disclosed methods of identifying the presence of archetype JC virus in a sample include detecting the entire "d" section in a nucleic acid molecule amplified from the biological sample.

Several embodiments include comparison of the presence (or absence or amount) of the first amplified nucleic acid (including some or all of the nucleic acids of the d section of the hypervariable region of the NCRR of Archetype JC virus) in a biological sample with the presence (or absence or amount) of the amplified second nucleic acid (including a nucleic acid sequence included in both Archetype and Prototype JC virus) in the biological sample. Thus, in some embodiments, detecting the presence of the first amplified nucleic acid molecule and the presence of the second amplified nucleic acid molecule detects the presence of Archetype JC virus in the biological sample. In some embodiments, detecting the absence of the first amplified nucleic acid molecule and the presence of the second amplified nucleic acid molecule detects the presence of Prototype JC virus in the biological sample. In some embodiments, detecting more of the amplified second nucleic acid molecule than the amplified first nucleic acid molecule identifies the presence of Prototype JC virus in the biological sample.

The skilled artisan will appreciate that detecting the presence or absence (or amount) of the first and second amplified nucleic acid molecules as described herein using PCR (such as qPCR) assays can include detecting the presence or absence (or amount) of the first and second nucleic acid molecules after a particular amplification cycle of the PCR (e.g., qPCR) assay. For example, after 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40 amplification cycles of the PCR (e.g., qPCR) assay, or at least that may cycles, or no more than that many cycles.

In several embodiments, detecting the presence of Prototype JC virus in the biological sample using a multiplex PCR (e.g., qPCR) assay includes detecting the presence of the second nucleic acid molecule in an earlier amplification cycle of the multiplex PCR (e.g., qPCR) assay than an amplification cycle in which the presence of the first nucleic acid molecule is detected. For example, detecting the presence of Prototype JC virus in the biological sample using a multiplex PCR (e.g., qPCR) assay can include detecting the presence of the second nucleic acid molecule in a amplification cycle of the PCR (e.g., qPCR) assay that is at least 1 (such as at least 2, 3, 4, 5, 6, 7, 8, 9, 10, 11, 12, 13, 14, 15, 16, 17, 18, 19, or at least 20, or no more than that many) amplification cycles earlier than an amplification cycle in which the presence of the first nucleic acid molecule is detected. In some embodiments, detecting the presence of Prototype JC virus in the biological sample using a multiplex PCR (e.g., qPCR) assay can include detecting the presence of the second nucleic acid molecule in a amplification cycle of the PCR (e.g., qPCR) assay that is at least 2 amplification cycles earlier than an amplification cycle in which the presence of the first nucleic acid molecule is detected. In some embodiments, the qPCR assay comprises two or more amplification cycles, and detecting the presence of Prototype JC virus in the biological sample comprises detecting the second nucleic acid molecule in an earlier amplification cycle of the qPCR assay than an amplification cycle in which the first nucleic acid molecule is detected.

In some examples, the disclosed methods can predict with a sensitivity of at least 90% and a specificity of at least 90% for the identity of Archetype or Prototype JC virus in a biological sample, such as a sensitivity of at least 91%, 92%, 93%, 94%, 95%, 96%, 97%, 98%, 99%, or even 100% and a specificity of at least of at least 91%, 92%, 93%, 94%, 95%, 96%, 97%, 98%, 99%, or even 100%.

Appropriate biological samples include all clinical samples useful for detection of disease or infection (e.g., JC virus infection) in subjects. Exemplary biological samples include, without limitation, cells, cell lysates, blood smears, cytocentrifuge preparations, cytology smears, bodily fluids (e.g., blood, plasma, serum, saliva, sputum, urine, bronchoalveolar lavage, semen, CSF, etc.), tissue biopsies or autopsies, fine-needle aspirates, and/or tissue sections. In one embodiment, the biological sample is a urine sample. In another embodiment, the biological sample is a serum sample. In a further embodiment, the biological sample is a CSF sample. In a particular example, a biological sample is obtained from a subject having, suspected of having or at risk of having, PML; for example, a subject having HIV infection or a subject being treated with natalizumab. Standard techniques for acquisition of such samples are available (see, e.g. Schluger et al., *J. Exp. Med.* 176:1327-33, 1992;

Bigby et al., *Am. Rev. Respir. Dis.* 133:515-18, 1986; Kovacs et al., *NEJM* 318:589-93, 1988; and Ognibene et al., *Am. Rev. Respir. Dis.* 129:929-32, 1984). The sample can be used directly or can be processed, such as by adding solvents, preservatives, buffers, or other compounds or substances.

In some embodiments, nucleic acids are isolated from the sample. DNA or RNA can be extracted using standard methods. For instance, rapid DNA preparation can be performed using a commercially available kit (e.g., the Qiagen Tissue Kit, Qiagen, Inc., Valencia, Calif.). The DNA preparation technique can be chosen to yield a nucleotide preparation that is accessible to and amenable to nucleic acid amplification.

1. Amplifying Archetype Specific JC Virus Nucleic Acid

Several embodiments include amplifying from a biological sample a first nucleic acid molecule including all or a portion of the nucleic acid sequence of the d section of the hypervariable region of the Archetype JC virus genome (such as nucleotides 115-180 of SEQ ID NO: 1). For example, amplification of at least 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65 or at all 66 consecutive nucleotides of the d section (such as nucleotides 115-180 of SEQ ID NO: 1) of the hypervariable region of the Archetype JC virus genome. The amplified first nucleic acid molecule can include a maximum length, for example, the amplified first nucleic acid molecule can be up to about 200 nucleic acids in length, such as up to about 150, 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 40, 48, 47, 46, 45, 44, 43, 42, 41, 40, 39, 38, 37, 36, 35, 34, 33, 32, 31 or 30 nucleic acids in length.

Amplification of the first nucleic acid molecule includes the use of a first oligonucleotide primer pair including a forward oligonucleotide primer and a reverse oligonucleotide primer, as disclosed herein for amplifying nucleotides of the d section of the hypervariable region of Archetype JC virus. In some embodiments, the forward oligonucleotide primer includes at least 12 consecutive nucleotides (such as at least 13, 14, 15, 16, 17, 18, 19, 20, 21, 22, 23, 24, 25, 26, 27, 28, 29 or 30 consecutive nucleotides, or from 12-15, 12-20, 12-25, 12-30, 12-35, 12-40, 12-45, 14-15, 14-16, 14-18, 14-20, 14-25, 14-30, 15-16, 15-18, 15-20, 15-25, 15-30, 15-35, 15-40, 15-45, 16-17, 16-18, 16-20, 16-22, 16-25, 16-30, 16-40, 16-50, 17-18, 17-20, 17-22, 17-25, 17-30, 18-19, 18-20, 18-22, 18-25, 18-30, 19-20, 19-22, 19-25, 19-30, 20-21, 20-22, 20-25, 20-30, 20-35, 20-40, 20-45, 21-22, 21-25, 21-30, 22-25, 22-30, 22-40, 22-50, 23-24, 23-25, 23-30, 24-25, 24-30, 25-35, 25-30, 25-35, 25-40, or 25-45 consecutive nucleotides) from the nucleotide sequence set forth as nucleotides 93 to 138 of SEQ ID NO: 1, or the complement thereof. Further, in some embodiments, the reverse oligonucleotide primer includes at least 12 consecutive nucleotides (such as at least 13, 14, 15, 16, 17, 18, 19, 20, 21, 22, 23, 24, 25, 26, 27, 28, 29, or 30 consecutive nucleotides, or from 12-15, 12-20, 12-25, 12-30, 12-35, 12-40, 12-45, 14-15, 14-16, 14-18, 14-20, 14-25, 14-30, 15-16, 15-18, 15-20, 15-25, 15-30, 15-35, 15-40, 15-45, 16-17, 16-18, 16-20, 16-22, 16-25, 16-30, 16-40, 16-50, 17-18, 17-20, 17-22, 17-25, 17-30, 18-19, 18-20, 18-22, 18-25, 18-30, 19-20, 19-22, 19-25, 19-30, 20-21, 20-22, 20-25, 20-30, 20-35, 20-40, 20-45, 21-22, 21-25, 21-30, 22-25, 22-30, 22-40, 22-50, 23-24, 23-25, 23-30, 24-25, 24-30, 25-35, 25-30, 25-35, 25-40, or 25-45 consecutive nucleotides) from the nucleotide sequence set forth as nucleotides 159 to 206 of SEQ ID NO: 1, or the complement thereof.

In some embodiments, the first oligonucleotide primer pair includes forward and reverse oligonucleotide primers including or consisting of any one of the forward or reverse oligonucleotide primers disclosed in Table 3 for amplifying Archetype JC virus d section nucleic acid sequences, respectively. In further embodiments, the first oligonucleotide primer pair includes forward and reverse oligonucleotide primers including or consisting of the complement of any one of the forward or reverse oligonucleotide primers disclosed in Table 3 for amplifying Archetype JC virus d section nucleic acid sequences, respectively.

In some embodiments, the first oligonucleotide primer pair includes a forward oligonucleotide primer including or consisting of a nucleotide sequence at least 90% identical (such as at least 91%, 92%, 93%, 94%, 95%, 96%, 97%, 98%, or 99% identical) to any one of the forward oligonucleotide primers disclosed in Table 3 for amplifying Archetype JC virus d section nucleic acid sequences, and/or a reverse oligonucleotide primer including or consisting of a nucleotide sequence at least 90% identical (such as at least 91%, 92%, 93%, 94%, 95%, 96%, 97%, 98%, or 99% identical) to any one of the reverse oligonucleotide primers disclosed in Table 3 for amplifying Archetype JC virus d section nucleic acid sequences. In some embodiments, the first oligonucleotide primer pair includes a forward oligonucleotide primer including or consisting of a nucleotide sequence at least 90% identical (such as at least 91%, 92%, 93%, 94%, 95%, 96%, 97%, 98%, or 99% identical) to the complement of any one of the forward oligonucleotide primers disclosed in Table 3 for amplifying Archetype JC virus d section nucleic acid sequences, and/or a reverse oligonucleotide primer including or consisting of a nucleotide sequence at least 90% identical (such as at least 91%, 92%, 93%, 94%, 95%, 96%, 97%, 98%, or 99% identical) to the complement of any one of the reverse oligonucleotide primers disclosed in Table 3 for amplifying Archetype JC virus d section nucleic acid sequences. The forward and reverse primers can be of a maximum length, as disclosed herein.

In some embodiments, the first oligonucleotide primer pair includes a forward oligonucleotide primer including or consisting of the nucleotide sequence set forth as nucleotides 119-134 of SEQ ID NO: 1, and/or a reverse oligonucleotide primer including or consisting of the nucleotide sequence complementary to the sequence set forth as nucleotides 159-180 of SEQ ID NO: 1. In additional embodiments, the first oligonucleotide primer pair includes a forward oligonucleotide primer including or consisting of the nucleotide sequence set forth as nucleotides 119-134 of SEQ ID NO: 1, and a reverse oligonucleotide primer including or consisting of the nucleotide sequence complementary to the sequence set forth as nucleotides 159-180 of SEQ ID NO: 1. In some embodiments, the first oligonucleotide primer pair includes a forward oligonucleotide primer including or consisting of the nucleotide sequence complementary to nucleotides 119-134 of SEQ ID NO: 1, and/or a reverse oligonucleotide primer including or consisting of the nucleotide sequence set forth as nucleotides 159-180 of SEQ ID NO: 1. In additional embodiments, the first oligonucleotide primer pair includes a forward oligonucleotide including or consisting of the nucleotide sequence complementary to nucleotides 119-134 of SEQ ID NO: 1, and a reverse oligonucleotide primer including or consisting of the nucleotide sequence set forth as nucleotides 159-180 of SEQ ID NO: 1. The forward and reverse primers can be of a maximum length, as disclosed herein.

2. Amplifying Nucleic Acid Sequence Present in Archetype and Prototype JC Virus

Several embodiments include amplifying from a biological sample a second nucleic acid molecule including a nucleic acid sequence of the JC virus genome present in both Archetype and Prototype JC virus. For example, amplifying from a biological sample a nucleic acid sequence that is present in both SEQ ID NO: 1 and SEQ ID NO: 2.

In some embodiments, the second nucleic acid molecule includes a nucleic acid sequence that is present in both Archetype and Prototype JC virus genome, wherein the second nucleic acid molecule is from the large T-antigen, small-t antigen, VP1, VP2, or VP3 segment of the JC virus genome. Amplification of the second nucleic acid molecule can include the use of a second oligonucleotide primer pair including a forward oligonucleotide primer and a reverse oligonucleotide primer designed for amplification of the second nucleic acid molecule.

The second nucleic acid molecule can include or consist of at least about 20, 25, 30, 35, 40, 45, 50, 60, 70, 80, 90, 100, 150 or 200 consecutive nucleotides of a nucleic acid sequence of the JC virus genome present in both Archetype and Prototype JC virus, such as a nucleic acid sequence that is present in both SEQ ID NO: 1 and SEQ ID NO: 2. In some examples the second nucleic acid includes about 20 consecutive nucleotides of a nucleic acid sequence of the JC virus genome present in both Archetype and Prototype JC virus, such as a nucleic acid sequence that is present in both SEQ ID NO: 1 and SEQ ID NO: 2. The amplified second nucleic acid molecule can include a maximum length, for example, the amplified second nucleic acid molecule can be up to about 200 nucleic acids in length, such as up to about 150, 100, 90, 80, 70, 60, 50, 45, 40, 35, 30 nucleic acids in length. In some embodiments, the amplified second nucleic acid molecule includes a maximum length about 50 nucleic acids in length. For example, in some embodiments, the second nucleic acid molecule includes at least 30 consecutive nucleic acids (such as at least 35, 40, 45, 50, 60, 70, 80, 90 100, 150 or 200 consecutive nucleotides) of nucleotides 2594-4417 of SEQ ID NO: 1 that is also present in SEQ ID NO: 2.

Amplification of the second nucleic acid molecule includes the use of a second oligonucleotide primer pair including a forward oligonucleotide primer and a reverse oligonucleotide primer designed to amplify a nucleic acid sequence of the JC virus genome present in both Archetype and Prototype JC virus, such as sequence present in both SEQ ID NO: 1 and SEQ ID NO: 2. In some embodiments, the first and second oligonucleotide primers of the second primer pair include or consist of at least about 10 consecutive nucleotides (such as at least about 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or about 50 consecutive nucleotides) from a nucleotide sequence present in both SEQ ID NO: 1 and SEQ ID NO: 2, or the complement thereof, respectively. For example, in some embodiments, the first and second oligonucleotide primers of the second primer pair include or consist of 10-50 consecutive nucleotides, such as, 12-15, 12-20, 12-25, 12-30, 12-35, 12-40, 12-45, 12-50, 14-15, 14-16, 14-18, 14-20, 14-25, 14-30, 15-16, 15-18, 15-20, 15-25, 15-30, 15-35, 15-40, 15-45, 15-50, 16-17, 16-18, 16-20, 16-22, 16-25, 16-30, 16-40, 16-50, 17-18, 17-20, 17-22, 17-25, 17-30, 18-19, 18-20, 18-22, 18-25, 18-30, 19-20, 19-22, 19-25, 19-30, 20-21, 20-22, 20-25, 20-30, 20-35, 20-40, 20-45, 20-50, 21-22, 21-25, 21-30, 22-25, 22-30, 22-40, 22-50, 23-24, 23-25, 23-30, 24-25, 24-30, 25-30, 25-35, 25-40, 25-45, or 25-50 consecutive nucleotides of nucleotide sequence present in both SEQ ID NO: 1 and SEQ ID NO: 2, or the complement thereof, respectively.

In some embodiments, the forward oligonucleotide primer is from 23-50 nucleotides in length (such as from 23-24, 23-25, or 23-30 nucleotides in length, such as 23, 24, 25, 26, 27, 28, 29, or 30 nucleotides in length), and includes the nucleotide sequence set forth as nucleotides 4291-4313 of SEQ ID NO: 1, and the reverse oligonucleotide primer is from 22-50 nucleotides in length (such as from 22-23, 22-25, or 22-30 nucleotides in length, such as 22, 23, 24, 25, 26, 27, 28, 29, or 30 nucleotides in length) and includes the complement of the nucleotide sequence set forth as nucleotides 4340-4361 of SEQ ID NO: 1. In some embodiments, the forward oligonucleotide primer is from 23-50 nucleotides in length (such as from 23-24, 23-25, or 23-30 nucleotides in length, such as 23, 24, 25, 26, 27, 28, 29, or 30 nucleotides in length), and includes the complement of the nucleotide sequence set forth as nucleotides 4291-4313 of SEQ ID NO: 1, and the reverse oligonucleotide primer is from 22-50 nucleotides in length (such as from 22-23, 22-25, or 22-30 nucleotides in length, such as 22, 23, 24, 25, 26, 27, 28, 29, or 30 nucleotides in length) and includes the nucleotide sequence set forth as nucleotides 4340-4361 of SEQ ID NO: 1.

In some embodiments, the second oligonucleotide primer pair includes a forward oligonucleotide primer including or consisting of a nucleic acid sequence at least 90% identical (such as at least 91%, 92%, 93%, 94%, 95%, 96%, 97%, 98%, or 99% identical) to the nucleotide sequence set forth as nucleotides 4291-4313 of SEQ ID NO: 1, and/or a reverse oligonucleotide primer including or consisting of a nucleic acid sequence at least 90% identical (such as at least 91%, 92%, 93%, 94%, 95%, 96%, 97%, 98%, or 99% identical) to the complement of the nucleotide sequence set forth as nucleotides 4340-4361 of SEQ ID NO: 1. In some embodiments, the second oligonucleotide primer pair includes a forward oligonucleotide primer including or consisting of a nucleic acid sequence at least 90% identical (such as at least 91%, 92%, 93%, 94%, 95%, 96%, 97%, 98%, or 99% identical) to the complement of the nucleotide sequence set forth as nucleotides 4291-4313 of SEQ ID NO: 1, and/or a reverse oligonucleotide primer including or consisting of a nucleic acid sequence at least 90% identical (such as at least 91%, 92%, 93%, 94%, 95%, 96%, 97%, 98%, or 99% identical) to the nucleotide sequence set forth as nucleotides 4340-4361 of SEQ ID NO: 1.

In additional embodiments, the second oligonucleotide primer pair includes a forward oligonucleotide primer including or consisting of the nucleotide sequence set forth as nucleotides 4291-4313 of SEQ ID NO: 1, and/or a reverse oligonucleotide primer including or consisting of the complement of the nucleotide sequence set forth as nucleotides 4340-4361 of SEQ ID NO: 1. In some embodiments, the second oligonucleotide primer pair includes a forward oligonucleotide primer including or consisting of the nucleotide sequence set forth as the complement of nucleotides 4291-4313 of SEQ ID NO: 1, and/or a reverse oligonucleotide primer including or consisting consists of the nucleotide sequence set forth as nucleotides 4340-4361 of SEQ ID NO: 1.

3. Detecting Amplified Nucleic Acid Sequences

In several embodiments, an oligonucleotide probe is used to detect amplified nucleic acids, such as the first and second amplified nucleic acids described above. The skilled artisan will appreciate that the oligonucleotide probe includes a nucleic acid sequence that hybridizes to the amplified nucleic acid molecule under stringent or highly stringent conditions, but does not include a nucleotide sequence that hybridizes under stringent or highly stringent conditions to the sequence of the oligonucleotide primers used to amplify the nucleic acid molecule.

In several embodiments, detecting the amplified first nucleic acid molecule described above includes use of an oligonucleotide probe including or consisting of at least 10 consecutive nucleotides of the nucleotide sequence set forth as nucleotides 115-180 of SEQ ID NO: 1, or the complement thereof. For example, the oligonucleotide probe can include at least 10 consecutive nucleotides, such as at least 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, or at least 66 consecutive nucleotides of the d section (nucleotides 115-180 of SEQ ID NO: 1) of the hypervariable region of the Archetype JC virus genome, including a probe with at least 75% (for example at least 85%, 90%, 95%, 96%, 97%, 98% or 99%) sequence identity to the JC virus sequences disclosed herein, such as SEQ ID NO: 1. In some embodiments, detecting the second nucleic acid molecule described above includes use of an oligonucleotide probe including or consisting of 10-50 consecutive nucleotides, such as 12-15, 12-20, 12-25, 12-30, 12-35, 12-40, 12-45, 12-50, 14-15, 14-16, 14-18, 14-20, 14-25, 14-30, 15-16, 15-18, 15-20, 15-25, 15-30, 15-35, 15-40, 15-45, 15-50, 16-17, 16-18, 16-20, 16-22, 16-25, 16-30, 16-40, 16-50, 17-18, 17-20, 17-22, 17-25, 17-30, 18-19, 18-20, 18-22, 18-25, 18-30, 19-20, 19-22, 19-25, 19-30, 20-21, 20-22, 20-25, 20-30, 20-35, 20-40, 20-45, 20-50, 21-22, 21-25, 21-30, 22-25, 22-30, 22-40, 22-50, 23-24, 23-25, 23-30, 24-25, 24-30, 25-35, 25-30, 25-35, 25-40, 25-45, or 25-50 consecutive nucleotides, of the d section (nucleotides 115-180 of SEQ ID NO: 1) of the hypervariable region of the Archetype JC virus genome. In some embodiments, detecting the first nucleic acid molecule includes use of an oligonucleotide probe including or consisting of the nucleotide sequence set forth as nucleotides 139-158 of SEQ ID NO: 1, or the complement thereof. In some embodiments, the probes can be of a maximum length, for example no more than 15, 25, 25, 40, 50, 75, 100, or 150 nucleotides in length.

In several embodiments, detecting the second nucleic acid molecule described above includes use of an oligonucleotide probe including or consisting of at least 10 consecutive nucleotides (such as at least 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 consecutive nucleotides) of the amplified second nucleic acid molecule. For example, in some embodiments, detecting the second nucleic acid molecule described above includes use of an oligonucleotide probe including or consisting of 10-100 nucleotides (such as 12-15, 12-20, 12-25, 12-30, 12-35, 12-40, 12-45, 12-50, 12-80, 14-15, 14-16, 14-18, 14-20, 14-25, 14-30, 15-16, 15-18, 15-20, 15-25, 15-30, 15-35, 15-40, 15-45, 15-50, 15-80, 16-17, 16-18, 16-20, 16-22, 16-25, 16-30, 16-40, 16-50, 17-18, 17-20, 17-22, 17-25, 17-30, 18-19, 18-20, 18-22, 18-25, 18-30, 19-20, 19-22, 19-25, 19-30, 20-21, 20-22, 20-25, 20-30, 20-35, 20-40, 20-45, 20-50, 20-80, 21-22, 21-25, 21-30, 22-25, 22-30, 22-40, 22-50, 23-24, 23-25, 23-30, 24-25, 24-30, 25-35, 25-30, 25-35, 25-40, 25-45, 25-50, or 25-80 consecutive nucleotides) of the amplified second nucleic acid molecule. In some embodiments, detecting the second nucleic acid molecule includes use of an oligonucleotide probe including or consisting of the nucleotide sequence set forth as nucleotides 4315-4330 of SEQ ID NO: 1, or the complement thereof. In some embodiments, the probes can be of a maximum length, for example no more than 15, 25, 25, 40, 50, 75, 100, or 150 nucleotides in length.

In several embodiments, the probe for detecting the first nucleic acid molecule does not hybridize to the primer pair used to amplify the first nucleic acid, and/or the primer pair used to amplify the second nucleic acid molecule, under stringent or highly stringent conditions. In several embodiments, the probe for detecting the second nucleic acid molecule does not hybridize to the primer pair used to amplify the first nucleic acid, and/or the primer pair used to amplify the second nucleic acid molecule, under stringent or highly stringent conditions In several embodiments, the oligonucleotide probe can be labeled, for example with a base-linked or terminally-linked fluorophore and non-fluorescent quencher for use in qPCR assays. Fluorophores for use in qPCR assays are known in the art. They can be obtained, for example, from Life Technologies (Gaithersburg, Md.), Sigma-Genosys (The Woodlands, Tex.), Genset Corp. (La Jolla, Calif.), or Synthetic Genetics (San Diego, Calif.). Fluorophores can be conjugated to the oligonucleotides, for example by post-synthesis modification of oligonucleotides that are synthesized with reactive groups linked to bases. Useful fluorophores include: fluorescein, fluorescein isothiocyanate (FITC), carboxy tetrachloro fluorescein (TET), NHS-fluorescein, 5 and/or 6-carboxy fluorescein (FAM), 5-(or 6-) iodoacetamidofluorescein, 5-{[2(and 3)-5-(Acetylmercapto)-succinyl]amino}fluorescein (SAMSA-fluorescein), 5'-hexachloro-fluorescein (HEX), 6-carboxy-4',5'-dichloro-2',7'dimethoxyfluorescein,succinimidyl ester (JOE) and other fluorescein derivatives, rhodamine, Lissamine rhodamine B sulfonyl chloride, Texas red sulfonyl chloride, 5 and/or 6 carboxy rhodamine (ROX) and other rhodamine derivatives, coumarin, 7-amino-methyl-coumarin, 7-Amino-4-methylcoumarin-3-acetic acid (AMCA), and other coumarin derivatives, BODIPY fluorophores, Cascade Blue fluorophores such as 8-methoxypyrene-1,3,6-trisulfonic acid trisodium salt, Lucifer yellow fluorophores such as 3,6-Disulfonate-4-amino-naphthalimide, phycobiliproteins derivatives, Alexa fluor dyes (available from Molecular Probes, Eugene, Oreg.) and other fluorophores known to those of skill in the art. For a general listing of useful fluorophores, see also Hermanson, G. T., BIOCONJUGATE TECHNIQUES (Academic Press, San Diego, 1996).

Quenchers for use in qPCR assays are also known in the art and include, for example, 6-carboxytetramethylrhodamine,succinidyl ester (6-TAMRA; TAMRA) and "non-fluorescent quencher (NFP)" for use with TAQMAN™ probes available from Life technologies.

4. PCR and Multiplex qPCR

Several embodiments include the use of PCR and/or qPCR. PCR reaction conditions typically include either two or three step cycles. Two step cycles have a denaturation step followed by a hybridization/elongation step. Three step cycles include a denaturation step followed by a hybridization step during which the primer hybridizes to the strands of DNA, followed by a separate elongation step. The polymerase reactions are incubated under conditions in which the primers hybridize to the target sequences and are extended by a polymerase. The amplification reaction cycle conditions are selected so that the primers hybridize specifically to the target sequence and are extended.

Primers are typically designed so that all of the primers participating in a particular reaction have melting temperatures that are within at least five degrees Celsius, and more typically within two degrees Celsius of each other. Primers are further designed to avoid priming on themselves or each other. Primer concentration should be sufficient to bind to the amount of target sequences that are amplified so as to provide an accurate assessment of the quantity of amplified sequence. Those of skill in the art will recognize that the amount of concentration of primer will vary according to the binding affinity of the primers as well as the quantity of sequence to be bound. Typical primer concentrations will range from 0.01 µM to 0.5 µM.

In a typical PCR cycle, a sample including a DNA polynucleotide and a PCR reaction cocktail is denatured by treatment in thermal cycler at about 90-98° C. for 10-90 seconds. The denatured polynucleotide is then hybridized to oligonucleotide primers by treatment in a thermal cycler at a temperature of about 30-65° C. for 1-2 minutes. Chain extension then occurs by the action of a DNA polymerase on the polynucleotide annealed to the oligonucleotide primer. This reaction occurs at a temperature of about 70-75° C. for 30 seconds to 5 minutes. Any desired number of PCR cycles may be carried out depending on variables including but not limited to the amount of the initial DNA polynucleotide, the length of the desired product and primer stringency. The above temperature ranges and the other numbers are exemplary and not intended to be limiting. These ranges are dependent on other factors such as the type of enzyme, the type of container or plate, the type of biological sample, the size of samples, etc. One of ordinary skill in the art will recognize that the temperatures, time durations and cycle number can readily be modified as necessary.

Several embodiments include quantitative real-time polymerase chain reaction (qPCR), which is used to simultaneously quantify and amplify a specific part of a given nucleic acid molecule. It is used, for example, to determine whether or not a specific sequence is present in the sample; and if it is present, the number of copies in the sample.

qPCR monitors the fluorescence emitted during the reaction as an indicator of amplicon production during each PCR cycle, as opposed to endpoint detection. The real-time progress of the reaction can be viewed in some systems. Typically, real-time PCR uses the detection of a fluorescent reporter. Typically, the fluorescent reporter's signal increases in direct proportion to the amount of PCR product in a reaction. By recording the amount of fluorescence emission at each cycle, it is possible to monitor the PCR reaction during exponential phase where the first significant increase in the amount of PCR product correlates to the initial amount of target template. The higher the starting copy number of the nucleic acid target, the sooner a significant increase in fluorescence is observed. Thus, the procedure follows the general pattern of polymerase chain reaction, but the nucleic acid molecule is quantified after each round of amplification. In several embodiments the amplified nucleic acid molecule is quantified by the use of fluorescent dye that intercalates with double-strand DNA. In other embodiments (e.g., when multiplex qPCR assays are utilized) amplified nucleic acid molecule is quantified by use of oligonucleotide probes labeled with a reporter fluorophore that can be detected in the qPCR assay.

In certain embodiments, the amplified products are directly visualized with detectable label such as a fluorescent DNA-binding dye. In one embodiment the amplified products are quantified using an intercalating dye, including but not limited to SYBR green, SYBR blue, DAPI, propidium iodine, Hoeste, SYBR gold, ethidium bromide, acridines, proflavine, acridine orange, acriflavine, fluorcoumanin, ellipticine, daunomycin, chloroquine, distamycin D, chromomycin, homidium, mithramycin, ruthenium polypyridyls, anthramycin. For example, a DNA binding dye such as SYBR green binds double stranded DNA and an increase in fluorescence intensity can be measured. For example, the fluorescent dsDNA dye can be added to the buffer used for a PCR reaction. The PCR assay can be performed in a thermal cycler, and after each cycle, the levels of fluorescence are measured with a detector, such as a camera. The dye fluoresces much more strongly when bound to dsDNA (e.g., amplified PCR product). Because the amount of the dye intercalated into the double-stranded DNA molecules is typically proportional to the amount of the amplified DNA products, the amount of amplified nucleic acid can be quantified by detecting the fluorescence of the intercalated dye using detection instruments known in the art. When referenced to a standard dilution, the dsDNA concentration in the PCR can be determined.

In addition to various kinds of fluorescent DNA-binding dye, other luminescent labels such as sequence specific oligonucleotide probes can be employed in the amplification reaction to facilitate the detection and quantification of the amplified product. Probe based quantitative amplification relies on the sequence-specific detection of a desired amplified product. Unlike the dye-based quantitative methods, it utilizes target-specific probe labeled with a detectable marker such as a base-linked or terminally-linked fluorophore and quencher. Such markers are known to the person of ordinary skill in the art and described herein. Further, methods for performing probe-based quantitative amplification are well established in the art (see, e.g., U.S. Pat. No. 5,210,015).

For detection using oligonucleotide probes, the reaction is prepared as usual for PCR conditions, with the addition of the sequence specific labeled oligonucleotide probe. After denaturation of the DNA, the labeled probe is able to bind to its complementary sequence in the region of interest of the template DNA. When the PCR reaction is heated to the proper extension temperature, the polymerase is activated and DNA extension proceeds. As the polymerization continues it reaches the labeled probe bound to the complementary sequence of DNA. The polymerase breaks the probe into separate nucleotides, and separates the fluorescent reporter from the quencher. This results in an increase in fluorescence as detected by the optical assembly. As PCR cycle number increases more and more of the fluorescent reporter is liberated from its quencher, resulting in a well-defined geometric increase in fluorescence. This allows accurate determination of the final, and initial, quantities of DNA.

In one embodiment, the fluorescently-labeled probes (such as probes disclosed herein) rely upon fluorescence resonance energy transfer (FRET), or in a change in the fluorescence emission wavelength of a sample, as a method to detect hybridization of a DNA probe to the amplified target nucleic acid in real-time. For example, FRET that occurs between fluorogenic labels on different probes (for example, using HybProbes) or between a donor fluorophore and an acceptor or quencher fluorophore on the same probe (for example, using a molecular beacon or a TAQMAN™ probe) can identify a probe that specifically hybridizes to the DNA sequence of interest. In some embodiments, the fluorescently-labeled DNA probes used to identify amplification products have spectrally distinct emission wavelengths, thus allowing them to be distinguished within the same reaction tube, for example in multiplex PCR, such as a multiplex real-time PCR.

Any type of thermal cycler apparatus can be used for the amplification of JCV virus nucleic acids as described above and/or the determination of hybridization. Examples of suitable apparatuses include PTC-100® Peltier Thermal Cycler (MJ Research, Inc.; San Francisco, Calif.), a ROBO-CYCLER® 40 Temperature Cycler (Agilent/Stratagene; Santa Clara, Calif.), or GeneAmp® PCR System 9700 (Applied Biosystems; Foster City, Calif.). For real-time PCR, any type of real-time thermocycler apparatus can be used. For example, ICYCLER IQ™ or CFX96™ real-time detection systems (Bio-Rad, Hercules, Calif.), LIGHTCYCLER® systems (Roche, Mannheim, Germany), a 7700 Sequence Detector (Perkin Elmer/Applied Biosystems; Foster City, Calif.), ABI™ systems such as the 7000, 7300, 7500, 7700, or 7900 systems (Applied Biosystems; Foster City, Calif.), or an MX4000™, MX3000™ or MX3005™ qPCR system (Agilent/Stratagene; Santa Clara, Calif.), DNA ENGINE OPTICON® Continuous Fluorescence Detection System (Bio-Rad, Hercules, Calif.), ROTOR-GENE® Q real-time cycler (Qiagen, Valencia, Calif.), or SMARTCYCLER® system (Cepheid, Sunnyvale, Calif.) can be used to amplify and detect nucleic acid sequences in real-time. In some embodiments, real-time PCR is performed using a TAQMAN® array format, for example, a microfluidic card in which each well is pre-loaded with primers and probes for a particular target. The reaction is initiated by adding a sample including nucleic acids and assay reagents (such as a PCR master mix) and running the reactions in a real-time thermocycler apparatus.

In several embodiments, multiplex qPCR assays are used to amplify and detect the first and second nucleic acid molecules as described above. In the multiplex qPCR assays, the first and second nucleic acids are amplified and detected in a single reaction. For example, the multiplex qPCR assay can include amplifying from a biological sample a first nucleic acid molecule including all or a portion of the d section of the hypervariable region of the Archetype JC virus genome (such as nucleotides 115-180 of SEQ ID NO: 1), and also amplifying from a biological sample a second nucleic acid molecule including a nucleic acid sequence of the JC virus genome present in both Archetype and Prototype JC virus (such as a nucleic acid sequence present in both SEQ ID NO: 1 and SEQ ID NO: 2).

In some embodiments, multiplex qPCR is performed using the Applied Biosystem 7500 Real-time PCR system and (ABI) Gene Expression Master mix (Cat #4369016). In one example, the multiplex real-time PCR can be performed in a total reaction volume of 50 µl containing 10 µl of DNA extract, 40 µl of 2×PCR master mix, the forward and reverse primers for the first oligonucleotide primer pair, the forward and reverse primers of the second oligonucleotide primer pair, and the first and second oligonucleotide probes corresponding to the first and second nucleic acid molecules amplified by the first and second oligonucleotide primer pairs, respectively. The concentration of both sets of primers can be 300 nM and the probes can be 200 nM. In some examples, the following protocol can be used for the multiplex qPCR: 50° C. for 2 minutes; 95° C. for 10 minutes; followed by 40 cycles of 95° C. for 15 seconds and 60° C. for 1 minute. Each multiplex qPCR assay can include a standard dilution series for DNA quantification. Further, samples can be analyzed in duplicate as part of a CLIA protocol. Negative reagent and extraction controls can be included with each assay along with positive controls of a known amount of JC viral plasmid for both Archetype and Prototype JC virus variants.

In some embodiments, amplification and detection of the first and second nucleic acid sequences in the multiplex qPCR assays can be performed using any of the oligonucleotide pairs and probes provided herein for amplification and detection of the first and second nucleic acid molecules, such as those described above and in Table 3, below.

Detection of the first and second nucleic acid sequences in multiplex qPCR assays is performed using a first oligonucleotide probes specific for the first nucleic acid sequence and a second oligonucleotide probe specific for the second nucleic acid sequence. For example, detection of the first nucleic acid molecule can include use of an oligonucleotide probe including a nucleotide sequence set forth as nucleotides 139-158 of SEQ ID NO: 1, or the complement thereof, and detection of the second nucleic acid molecule can include use of an oligonucleotide probe including a nucleotide sequence set forth as nucleotides 4315-4330 of SEQ ID NO: 1, or the complement thereof.

In multiplex qPCR assays, the oligonucleotide probes used for detecting the first and second nucleic acid molecules are labeled with detectable markers that can be differentially detected in the same assay using detection equipment available to the person of ordinary skill in the art. For example, the oligonucleotide probe for detecting the first nucleic acid can be labeled with a first fluorophore and quencher and the oligonucleotide probe for detecting the second nucleic acid can be labeled with a second fluorophore and quencher, wherein the first and second baselinked or terminally-linked fluorophore and quencher can be differentially detected.

In one example, the first and second oligonucleotide probes are labeled with TAQMAN™ fluorophores and quenchers that can be differentially detected, such as fluorophores and quenchers available from Applied Biosystems by Life Technologies, Carlsbad, Calif.). In one example, the oligonucleotide probe for detecting the first nucleic acid sequence is labeled with the VIC fluorophore and the NFQ™ quencher available from Applied Biosystems by Life Technologies, Carlsbad, Calif., and the oligonucleotide probe for detecting the second nucleic acid is labeled with the 6-carboxyfluorescin (FAM) fluorophore and the NFQ™ quencher available from Applied Biosystems by Life Technologies, Carlsbad, Calif.

IV. Diagnostic and Therapeutic Methods

Several embodiments relate to identifying and managing the therapeutic treatment of subjects who are at an increased risk of PML. PML can be caused by JC virus infection, particularly in subjects having a weakened immune system, such as a subject with an immunosuppressive disorder, or a subject being treated with an immunosuppressive agent (such as a chemotherapeutic agent). However, PML does not develop in all JC virus-infected subjects, or all JC infected subjects having a weakened immune system. One indicator of an increased risk of PML in a subject, such as a subject with a weakened immune system, is the presence of Prototype JC virus in the subject. Accordingly, in some embodiments, detecting the presence of Prototype JC virus in a biological sample from a subject using the methods provided herein identifies that subject as having an increased risk of developing PML.

In several embodiments, the provided methods of detecting the presence of Archetype and/or Prototype JC virus can be used to assist a clinician in selection of a therapy for a subject in need of immunosuppressive therapy (e.g., a subject with multiple sclerosis, or other disorder that can be treated with immunosuppressant agents). For example, in some embodiments, the disclosed methods of detecting the presence of Prototype and/or Archetype JC virus can be used to identify subjects that are at risk of developing PML prior to initiation of treatment with an immunosuppressive agent. If the subject is identified as having Prototype JC virus (e.g., by detection of Prototype JC virus in a CSF, plasma or urine sample from the subject as described herein), then the subject is not treated with immunosuppressive agents, treated with a low dosage of immunosuppressive agent and/or monitored closely for early symptoms of PML. If early symptoms of PML appear in the subject, the immunosuppressive treatment can be stopped, or the dosage of immunosuppressive agent can be reduced.

In some embodiments, a subject receiving immunosuppressant therapy (e.g., subject with multiple sclerosis, receiving treatment with an immunosuppressant agent) can be monitored for the presence of Prototype JC virus. If the subject is identified as having Prototype JC virus (e.g., by detection of Prototype JC virus in a CSF, plasma or urine sample from the subject as described herein), then the treatment with immunosuppressive agent can be halted, a reduced dose of the immunosuppressive agent can be used and/or monitored closely for early symptoms of PML. If early symptoms of PML appear in the subject, the immunosuppressive treatment can be stopped, or the dosage of immunosuppressive agent can be reduced. In some embodiments, the subject can be monitored for the presence of Prototype JC virus daily, weekly, biweekly, monthly, bi-monthly, quarterly, or annually.

In additional embodiments the disclosed methods can be used to identify a subject for treatment with an anti-PML agent. For example, the presence or absence of Prototype JC virus in a biological sample from the subject can be determined using the methods provided herein. If the presence of Prototype JC virus is detected in the biological sample, then the subject is identified as subject for treatment with an anti-PML agent. Exemplary anti-PML agents include cytosine arabinoside (ARA C) (see, for example, Aksamit, J Neurovirol., 7:386-390, 2001) and cidofovir (see, for example, Segarra-Newnham and Vodolo, Ann Pharmacther, 35:741-744, 2001). In some embodiments, about 1-10 mg/kg/day ARA C or cidofovir is administered to the subject, for example about 1, 2, 3, 4, 5, 6, 7, 8, 9, or 10 mg/kg/day ARA C or cidofovir can be administered to the subject. In some examples, a course of treatment with ARA C or cidofovir is administered to the subject, for example a course of treatment for 1, 2, 3, 4, 5, 6, 7, 8, 9, 10, 11, 12, 13, 14, 15, 16, 17, 18 or 20 consecutive days or 1, 2, 3, 4, 5, 6, 7, 8, 9, or 10 consecutive weeks, or 1, 2, 3, 4, 5, 6, 7, 8, 9, 10, 11 or 12 consecutive months. non-consecutive period of treatment may also be used.

In several embodiments, the disclosed methods of detecting the presence of Prototype and/or Archetype JC virus in a biological sample can be used to assist a clinician in selection and/or monitoring of a therapy for a subject with an underlying risk of developing PML, including for example, a subject with a weakened immune system, such as a subject with a neoplasm or an autoimmune disorder. Examples of subjects with a weakened immune system include subjects having, e.g., chemotherapy treatment, radiation treatment, radiation sickness, HIV infection or AIDs; conditions associated with primary B-cell deficiency (such as, e.g., Bruton's congenital a-γ-globulinemia or common variable immunodeficiency) or primary T-cell deficiency (such as, e.g., the DiGeorge and Nezelof syndromes, ataxia telangiectasia or Wiskott-Aldrich syndrome); severe combined immunodeficiency (SCID), autoimmune disorders, neoplasms, subjects being treated with an immunosuppressive agent, etc.

In some examples, a subject with a weakened immune system is a subject with a neoplasm such as a solid neoplasm, such as a sarcoma or carcinoma, including fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, sebaceous gland carcinoma, papillary carcinoma, papillary adenocarcinoma, medullary carcinoma, bronchogenic carcinoma, renal cell carcinoma, hepatoma, bile duct carcinoma, choriocarcinoma, Wilms' tumor, cervical cancer, testicular tumor, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma).

In other examples, a subject with a weakened immune system is a subject with a neoplasm including an abnormal cell growth occurring in a hematological cancer, including leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms; including Burkitt's lymphoma and mantle cell lymphoma), multiple myeloma, plasmacytoma, Waldenstrom's macroglobulinemia, heavy chain disease, myelodysplastic syndrome, sarcoidosis, and myelodysplasia.

In other examples, a subject with a weakened immune system is a subject with an autoimmune disorder, such as rheumatoid arthritis (RA), juvenile oligoarthritis, collagen-induced arthritis, adjuvant-induced arthritis, Sjogren's syndrome, multiple sclerosis (MS), experimental autoimmune encephalomyelitis (EAE), inflammatory bowel disease (e.g. Crohn's disease, ulceritive colitis), autoimmune gastric atrophy, pemphigus vulgaris, psoriasis, vitiligo, type I diabetes, non-obese diabetes, myasthenia gravis, Grave's disease, Hashimoto's thyroiditis, sclerosing cholangitis, sclerosing sialadenitis, systemic lupus erythematosis, autoimmune thrombocytopenia purpura, Goodpasture's syndrome, Addison's disease, systemic sclerosis, polymyositis, dermatomyositis, autoimmune hemolytic anemia pernicious anemia, and the like.

In several embodiments, the subject is a subject being treated with a therapeutic agent, such as natalizumab (Biogen Idec, Weston, Mass.), rituximab (Genetech, South San Francisco, Calif.), efalizumab (Genetech, South San Francisco, Calif.), brentuximab vedotin (Seattle Genetics, Seattle Wash.), fingolimod (Novartis AG, Basal, CH), mycophenolate mofetil (Genetech, South San Francisco, Calif.).

In additional embodiments, the disclosed methods can be used to detect Archetype and/or Prototype JC virus in a tissue for transplant into a subject in need thereof. For example, the methods can be used for the detection of Prototype and/or Archetype JC virus in an organ (such as a kidney, a lung, a heart, a pancreas, or other organ) that is to be transplanted into a subject (such as a subject in need of kidney of a kidney transplant). In several such embodiments, the transplant recipient is a subject with an compromised immune system.

V. Isolated Probes and Primers

Isolated oligonucleotide probes (which as defined herein also include the complementary sequence and corresponding RNA sequences) of use for the identification of Archetype and/or Prototype JC virus in a biological sample from a subject using the methods disclosed herein, and compositions comprising such probes and primers, are provided herein.

The isolated oligonucleotide probes include or consist of at least about 10 consecutive nucleotides, such as at least about 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or about 100 consecutive nucleotides from an Archetype or Prototype JC virus sequence, such as SEQ ID NOs: 1 or 2, including nucleic acid sequences having at least 75% (for example at least 85%, 90%, 95%, 96%, 97%, 98%, or 99%) sequence identity to a JC virus sequence, such as SEQ ID NO: 1 or SEQ ID NO: 2. For example, in some embodiments, the isolated oligonucleotide probe can include or consist of 10-100 consecutive nucleotides, such as, 12-15, 12-20, 12-25, 12-30, 12-35, 12-40, 12-45, 12-50, 12-80, 14-15, 14-16, 14-18, 14-20, 14-25, 14-30, 15-16, 15-18, 15-20, 15-25, 15-30, 15-35, 15-40, 15-45, 15-50, 15-80, 16-17, 16-18, 16-20, 16-22, 16-25, 16-30, 16-40, 16-50, 17-18, 17-20, 17-22, 17-25, 17-30, 18-19, 18-20, 18-22, 18-25, 18-30, 19-20, 19-22, 19-25, 19-30, 20-21, 20-22, 20-25, 20-30, 20-35, 20-40, 20-45, 20-50, 20-80, 21-22, 21-25, 21-30, 22-25, 22-30, 22-40, 22-50, 23-24, 23-25, 23-30, 24-25, 24-30, 25-35, 25-30, 25-35, 25-40, 25-45, 25-50, or 25-80 consecutive nucleotides from an Archetype or Prototype JC virus sequence, such as SEQ ID NO: 1 or SEQ ID NO: 2, including nucleic acid sequences having at least 75% (for example at least 85%, 90%, 95%, 96%, 97%, 98%, or 99%) sequence identity to a JC virus sequence, such as SEQ ID NO: 1 or SEQ ID NO: 2.

The isolated oligonucleotide primers include or consist of at least about 10 consecutive nucleotides, or at least about 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or about 50 consecutive nucleotides from an Archetype or Prototype JC virus sequence disclosed herein, such as SEQ ID NO: 1 or SEQ ID NO: 2, including nucleic acid sequences having at least 75% (for example at least 85%, 90%, 95%, 96%, 97%, 98% or 99%) sequence identity to a JC virus sequence, such as SEQ ID NO: 1 or SEQ ID NO: 2. For example, in some embodiments, the isolated oligonucleotide primers can include or consist of 10-50 nucleotides, such as, 12-15, 12-20, 12-25, 12-30, 12-35, 12-40, 12-45, 12-50, 14-15, 14-16, 14-18, 14-20, 14-25, 14-30, 15-16, 15-18, 15-20, 15-25, 15-30, 15-35, 15-40, 15-45, 15-50, 16-17, 16-18, 16-20, 16-22, 16-25, 16-30, 16-40, 16-50, 17-18, 17-20, 17-22, 17-25, 17-30, 18-19, 18-20, 18-22, 18-25, 18-30, 19-20, 19-22, 19-25, 19-30, 20-21, 20-22, 20-25, 20-30, 20-35, 20-40, 20-45, 20-50, 21-22, 21-25, 21-30, 22-25, 22-30, 22-40, 22-50, 23-24, 23-25, 23-30, 24-25, 24-30, 25-30, 25-35, 25-40, 25-45, or 25-50 consecutive nucleotides from an Archetype or Prototype JC virus sequence, such as SEQ ID NO: 1 or SEQ ID NO: 2, including nucleic acid sequences having at least 75% (for example at least 85%, 90%, 95%, 96%, 97%, 98%, or 99%) sequence identity to a JC virus sequence, such as SEQ ID NO: 1 or SEQ ID NO: 2.

In some embodiments, any of the probes or primers disclosed herein can be of a maximum length, for example no more than 15, 25, 25, 40, 50, 75, 100, or 150 nucleotides in length. Any of the isolated nucleic acid sequences disclosed herein may consist or consist essentially of the disclosed sequences, or include nucleic acid molecules that have a maximum length of 15, 20, 25, 30, 35, 40, 45, 50, 55, 60, 65, 70, 75 or 80 contiguous nucleotides of the disclosed sequence. The disclosed contiguous sequences may also be joined at either end to other unrelated sequences.

In some embodiments, the oligonucleotide probes and primers include or consist of the sequence of any one of the probes or primers listed above, or any one of the probers and primers listed in Table 3, below. These oligonucleotides can be employed as effective DNA hybridization probes or primers useful for amplification and/or detection of JC virus sequences.

Those versed in the art will recognize that specification of a single-stranded DNA sequence implies the utility of the complementary DNA sequence, as well as the two equivalent RNA sequences, for detecting viral differences, such as the differences between the NCRR of Archetype and Prototype JC virus. Furthermore, sequences incorporating modifications of any of the moieties including the nucleic acid (such as the sugar or the backbone) are functional equivalents of the sequence. These sequences (or subsequences thereof) can themselves serve as probes or primers.

VI. Compositions

Compositions comprising one or more of the probes or primers disclosed herein are also provided. The compositions are useful, for example, in the disclosed methods of detecting the presence of Archetype and/or Prototype JC virus in a biological sample from a subject.

For example, the composition can include a first oligonucleotide primer pair for amplifying the first nucleic acid sequence as described above and/or a second oligonucleotide primer pair for amplifying the second nucleic acid molecules as described above. In additional embodiments, the composition includes a first oligonucleotide probe for detecting the first nucleic acid molecule as described above and/or a second oligonucleotide probe for detecting the second nucleic acid molecule as described above.

In some embodiments, the composition includes a first oligonucleotide primer pair including a forward oligonucleotide primer including or consisting of at least 12 consecutive nucleotides of the nucleotide sequence set forth as nucleotides 93 to 138 of SEQ ID NO: 1, and/or a reverse oligonucleotide primer including or consisting of at least 12 consecutive nucleotides complementary to the nucleotide sequence set forth as nucleotides 159 to 206 of SEQ ID NO: 1. In some embodiments, the forward oligonucleotide primer includes or consists of the nucleotide sequence set forth as nucleotides 119-134 of SEQ ID NO: 1, and/or the reverse oligonucleotide primer includes or consists of the nucleotide sequence complementary to the nucleotide sequence set forth as nucleotides 159-180 of SEQ ID NO: 1. In additional embodiments, the composition further includes a first oligonucleotide probe including 15 to 50 consecutive nucleotides of the nucleotide sequence amplified by the first oligonucleotide primer pair, e.g., the nucleic acid sequence set forth as nucleotides 115-180 of SEQ ID NO: 1, or the complement thereof. In one example, composition includes a first oligonucleotide probe including or consisting of the nucleotide sequence set forth as nucleotides 139-158 of SEQ ID NO: 1, or the complement thereof.

In some embodiments, the composition includes a second oligonucleotide primer pair including a forward oligonucleotide primer including or consisting of the nucleotide sequence set forth as nucleotides 4291-4313 of SEQ ID NO: 1, and/or a reverse oligonucleotide primer including or consisting of the nucleotide sequence set forth as nucleotides 4340-4361 of SEQ ID NO: 1. In additional embodiments, the composition further includes a second oligonucleotide probe including 15 to 50 consecutive nucleotides of the nucleotide sequence amplified by the second oligonucleotide primer pair, e.g., 15 to 50 consecutive nucleotides of the nucleotide sequence set forth as nucleotides 4313 to 4340 of SEQ ID NO: 1, or the complement thereof. In one example, the second oligonucleotide probe includes or consists of the nucleotide sequence set forth as nucleotides 4315-4330 of SEQ ID NO: 1, or the complement thereof.

In some embodiment, the composition includes a first oligonucleotide primer pair including a forward oligonucleotide primer including or consisting of the nucleotide sequence set forth as nucleotides 119-134 of SEQ ID NO: 1, and a reverse oligonucleotide primer including or consisting of the nucleotide sequence complementary to nucleotides 159-180 of SEQ ID NO: 1; a first oligonucleotide probe including or consisting of the nucleotide sequence set forth as nucleotides 139-158 of SEQ ID NO: 1, or the complement thereof; a second oligonucleotide primer pair including a forward oligonucleotide primer including or consisting of the nucleotide sequence set forth as nucleotides 4291-4313 of SEQ ID NO: 1, and a reverse oligonucleotide primer including or consisting of the nucleotide sequence complementary to nucleotides 4340-4361 of SEQ ID NO: 1; and a second oligonucleotide probe including or consisting of the nucleotide sequence set forth as nucleotides 4315-4330 of SEQ ID NO: 1, or the complement thereof.

In another embodiment, the composition includes a first oligonucleotide primer pair including a forward oligonucleotide primer including or consisting of the nucleotide sequence complementary to nucleotides 119-134 of SEQ ID NO: 1, and a reverse oligonucleotide primer including or consisting of the nucleotide sequence set forth as nucleotides 159-180 of SEQ ID NO: 1; a first oligonucleotide probe including or consisting of the nucleotide sequence set forth as nucleotides 139-158 of SEQ ID NO: 1, or the complement thereof; a second oligonucleotide primer pair including a forward oligonucleotide primer including or consisting of the nucleotide sequence complementary to nucleotides 4291-4313 of SEQ ID NO: 1, and a reverse oligonucleotide primer including or consisting of the nucleotide sequence set forth as nucleotides 4340-4361 of SEQ ID NO: 1; and a second oligonucleotide probe including or consisting of the nucleotide sequence set forth as nucleotides 4315-4330 of SEQ ID NO: 1, or the complement thereof.

VI. Kits

The oligonucleotide probes and/or primers and compositions including such probes and/or primers disclosed herein can be supplied in the form of a kit for use in identification of Archetype and/or Prototype JC virus in a biological sample. In such a kit, one or more of the oligonucleotide probes and/or primers is provided in one or more containers. An oligonucleotide probe or primer can be provided suspended in an aqueous solution, or as a freeze-dried or lyophilized powder. The container(s) in which the oligonucleotide(s) are supplied can be any conventional container that is capable of holding the supplied form; e.g., microfuge tubes, ampoules, or bottles. In some applications, pairs of primers can be provided in pre-measured single use amounts in individual, typically disposable, tubes or equivalent containers. With such an arrangement, the sample to be tested for the identification of Archetype or Prototype JC virus nucleic acids can be added to the individual tubes and amplification carried out directly, followed by sequence analysis, if desired or warranted but not necessary.

In some embodiments, the kit includes a container including a first oligonucleotide primer pair including a forward oligonucleotide primer and a reverse oligonucleotide primer, wherein the forward oligonucleotide primer comprises at least 12 consecutive nucleotides from the nucleotide sequence set forth as nucleotides 93 to 138 of SEQ ID NO: 1 and wherein the reverse oligonucleotide primer comprises at least 12 consecutive nucleotides complementary to the nucleotide sequence set forth as nucleotides 159 to 206 of SEQ ID NO: 1. The container can further include a second oligonucleotide primer pair including a forward oligonucleotide primer and a reverse oligonucleotide primer, wherein the forward oligonucleotide primer is 24 to 50 nucleotides in length and includes the nucleotide sequence set forth as nucleotides 4291-4313 of SEQ ID NO: 1, and the reverse oligonucleotide primer is 22 to 50 nucleotides in length and includes the nucleotide sequence set forth as nucleotides 4340-4361 of SEQ ID NO: 1. In additional embodiments, the container can further include a first oligonucleotide probe including 15 to 50 consecutive nucleotides of the nucleotide sequence set forth as nucleotides 115-180 of SEQ ID NO: 1, or the complement thereof and a second oligonucleotide probe including 15 to 50 consecutive nucleotides of the nucleotide sequence set forth as nucleotides 4313 to 4340 of SEQ ID NO: 1, or the complement thereof. The first oligonucleotide primer pair, the second oligonucleotide primer pair, the first oligonucleotide probe and the second oligonucleotide probe are formulated for use in a multiplex qPCR assay.

In some embodiments, the kit includes a container including a first oligonucleotide primer pair including a forward oligonucleotide primer and a reverse oligonucleotide primer, wherein the forward oligonucleotide primer consists of the nucleotide sequence set forth as nucleotides 119-134 of SEQ ID NO: 1, and wherein the reverse oligonucleotide primer consists of the nucleotide sequence complementary to the nucleotide sequence set forth as nucleotides 159-180 of SEQ ID NO: 1. The container can further include a second oligonucleotide primer pair including a forward oligonucleotide primer and a reverse oligonucleotide primer, wherein the forward oligonucleotide primer consists of the nucleotide sequence set forth as nucleotides 4291-4313 of SEQ ID NO: 1, and the reverse oligonucleotide primer consists of the nucleotide sequence set forth as nucleotides 4340-4361 of SEQ ID NO: 1. In additional embodiments, the container can further include a first oligonucleotide probe consists of the nucleotide sequence set forth as nucleotides 115-180 of SEQ ID NO: 1, or the complement thereof and a second oligonucleotide probe consists of the nucleotide sequence set forth as nucleotides 4313 to 4340 of SEQ ID NO: 1, or the complement thereof. The first oligonucleotide primer pair, the second oligonucleotide primer pair, the first oligonucleotide probe and the second oligonucleotide probe are formulated for use in a multiplex qPCR assay.

In some embodiments, kits can also include the reagents necessary to carry out PCR amplification reactions (including qPCR reactions), including DNA sample preparation reagents, appropriate buffers (e.g., polymerase buffer), salts (e.g., magnesium chloride), and deoxyribonucleotides (dNTPs). One or more control sequences for use in the PCR reactions can also be supplied in the kit.

In one embodiment, kits are supplied with instructions. In one specific, non-limiting example, the instructions are written instructions. In another such example, the instructions are provided in electronic format. The instructions may, for example, instruct the user how to use the primers and probes to amplify and detect the nucleic acid sequences using a qPCR reaction, and then differentiate the Archetype and Prototype JC virus using the methods described herein.

EXAMPLES

The following examples are provided to illustrate particular features of certain embodiments, but the scope of the claims should not be limited to those features exemplified.

Example 1

Materials and Methods Used in Example 2 and 3

Primers and Probes—
JCT primers are in the same location of the N-terminus of the viral T protein region as the primers used in the Clinical Laboratory Improvement Amendment (CLIA) protocol (Ryschkewitsch et al., *J Virol Methods.* 121:217-221, 2004, incorporated herein by reference in its entirety) except that the multiplex primers were designed to be two nucleotides shorter. The T protein internal probe is labeled with a fluorescent reporter dye 6-carboxyfluorescin (FAM) at the 5' end and a nonfluorescent quencher MGB (minor grove binding), at the 3' end. JRR primers span the D region (66 base pair insert) as described (Yogo et al., *J. Virol.*, 64:3139-43, 1990) (FIG. 1) minus four base pairs, which is consistent with the known Archetype sequence. The regulatory region internal probe is labeled with a nonfluorescent reporter dye (VIC), at the 5' end and a nonfluorescent quencher MGB (minor grove binding) at the 3'end synthesized to specifications by Applied Biosystems by Life Technologies, Carlsbad, Calif. The numbered location and sequence of each are shown in FIG. 1 with the complete viral genome map. Table 3 provides the sequences of probes and primers used in these assays.

TABLE 3

Sequences of Probes and Primers

| Identifier | Specificity | Type | Sequence (5'-3') | SEQ ID NO: 1 nucleotides |
|---|---|---|---|---|
| JRR-1 | Archetype | F. Primer | GGAGCCCTGGCTGCAT (SEQ ID NO: 3) | 119-134 |
| JRR-1.2 | Archetype | F. Primer | AGAGGGAGCCCTGGCTGCATGCCA (SEQ ID NO: 18) | 115-138 |
| JRR-1.3 | Archetype | F. Primer | CAGCCAGAGGGAGCCCTGGCTGCATGCCA (SEQ ID NO: 19) | 109-138 |
| JRR-1.4 | Archetype | F. Primer | GCTGACAGCCAGAGGGAGCCCTGGCTGCATGCCA (SEQ ID NO: 20) | 104-138 |
| JRR-1.5 | Archetype | F. Primer | AACCAGCTGACAGCCAGAGGGAGCCCTGGCTGCATGCCA (SEQ ID NO: 21) | 99-138 |
| JRR-1.6 | Archetype | F. Primer | GGAGCCAACCAGCTGACAGCCAGAGGGAGCCCTGGCTGCATGCCA (SEQ ID NO: 22) | 93-138 |
| JRR-1.1 | Archetype | Probe | CTGGCAGTTATAGTGAAACC (SEQ ID NO: 23) | 139-158 |
| JRR-2 | Archetype | R. Primer | TGTGATTAAGGACTATGGGAGG (SEQ ID NO: 4) | Complementary to 159-180 |
| JRR-3 | Archetype | R. Primer | TTACTTGTGATTAAGGACTATGGGAGG (SEQ ID NO: 24) | Complementary to 159-185 |
| JRR-4 | Archetype | R. Primer | CTTTGTTTACTTGTGATTAAGGACTATGGGAGG (SEQ ID NO: 25) | Complementary to 159-191 |
| JRR-5 | Archetype | R. Primer | CCTTGTGCTTTGTTTACTTGTGATTAAGGACTATGGGAGG (SEQ ID NO: 26) | Complementary to 159-198 |
| JRR-6 | Archetype | R. Primer | CTTCCCCTTGTGCTTTGTTTACTTGTGATTAAGGACTATGGGAGG (SEQ ID NO: 27) | Complementary to 159-203 |
| JRR-7 | Archetype | R. Primer | CCACTTCCCCTTGTGCTTTGTTTACTTGTGATTAAGGACTATGGGAGG (SEQ ID NO: 28) | Complementary to 159-206 |
| JCT-3 | Non-specific | F. Primer | AGTGTTGGGATCCTGTGTTTTCA (SEQ ID NO: 6) | 4291-4313 |
| JCT-1.2 | Non-specific | Probe | CATCACTGGCAAACAT (SEQ ID NO: 8) | 4315-4330 |
| JCT-4 | Non-specific | R. Primer | GTGGGATGAAGACCTGTTTTGC (SEQ ID NO: 7) | Complementary to 4340-4361 |

In Table 3, "F.Primer" refers to forward primer and "R.Primer" refers to reverse primer. ""Non-specific" specificity refers to a probe or primer having a nucleotide sequence included in both Archetype and Prototype JC virus. "Archetype" specificity refers to a probe or primer having a nucleotide sequence included in Archetype, but not Prototype JC virus.

For qPCR, the multiplex assay includes a specific fluorescent, dye-labeled probe for each sequence. The probes contain different fluorescent reporter dyes (FAM and VIC TAQMAN™ reporter dyes available from Life Technologies) to differentiate the amplification of T region or NCRR sequence. During PCR, each probe anneals specifically to complementary sequences between the forward and reverse primer sites. The DNA polymerase can cleave only probes that hybridize to the specific sequence. Cleavage separates the reporter dye from the nonquencher dye, which results in increased fluorescence by the reporter dye. As PCR cycling continues the absolute copy number of viral genomes in each sample is determined by assaying the fluorescence levels compared with those of the standard curve generated from known copy numbers of viral positive plasmid. Concentration of each sample was calculated using the ABI software (Applied Biosystems) and adjusted for dilution factors and reported out as copies/ml. The sensitivity of the T antigen multiplex assay is equal to the CLIA certified qPCR assay of 10 copies/ml (Ryschkewitsch et al., *J Virol Methods*. 121:217-221, 2004). The use of a nonfluorescent quencher at the 3' end (minor groove binder) increases the melting temperature of the probes allowing the use of shorter probes. The greater differences in the melting temperatures between the different probes provides more accurate specificity. Also the use of a nonfluorescent quenchers enables the machine to make more precise measurements of the dye contributions.

Positive Control and Standard Plasmids—

For the Prototype, pathogenic variant JC virus plasmid the complete sequence of the MAD1 strain pM1TC was used (SEQ ID NO: 2) (Frisque, et al., *J. Virol.*, 51:458-69, 1984, incorporated herein by reference). For the Archetype JC virus plasmid the complete sequence of the pCY (SEQ ID NO: 1) (Yogo et al., *J. Virol.*, 64:3139-43, 1990, incorporated herein by reference) was used. The DNA concentration for each of the plasmids ranged from 100 pg to 10 ag (attograms) in decreasing 10 fold serial dilutions to construct a standard curve.

DNA Extraction—

For CSF, serum, and plasma, viral DNA was extracted from 200-ul samples by using the QIAAMP MINELUTE™ kit (cat#57704) (Qiagen, Hilden, Germany) and then eluted in 25 µl of elution buffer. For urine, viral DNA was extracted from 200-µl samples by using AVL buffer (viral lysis buffer) (cat#19073) and then following the QIA MINELUTE™ kit. Cellular DNA was extracted up to a maximum of 5.0 (Yogo et al., *J. Virol.*, 64:3139-43, 1990) cells per sample using the Qiagen™ blood and tissue kit (Cat#69504) also eluting to a final volume of 25 µl using the mini-elute column.

Multiplex Real-Time qPCR—

Multiplex Real-time qPCR was performed using the Applied Biosystem 7500 Real-time PCR system and (ABI) Gene Expression Master mix (Cat #4369016). The Multiplex real-time PCR was performed in a total reaction volume of 50 µl containing 10 µl of DNA extract, 40 µl of 2×PCR master mix, each forward and reverse primer, and each probe. The concentration of both sets of primers were 300 nM and the probes were 200 nM. The PCR program was the following protocol: 50° C. for 2 minutes; 95° C. for 10 minutes; followed by 40 cycles of 95° C. for 15 seconds and 60° C. for 1 minute. Each multiplex PCR contained a standard dilution series for DNA quantification. All samples are analyzed in duplicate as part of the CLIA protocol. Negative reagent and extraction controls were included with each run along with positive controls of a known amount of viral plasmid for both Archetype and Prototype variants.

Multiplex Dual Spiking Experiments for Specificity—

DNA spiking experiments were conducted to test whether different concentrations of the two variants in the same sample influence the amplification efficiency of either variant. Plasmid standards diluted in water (FIG. 3) were spiked into DNA extraction solution from either CSF, PBMC, urine, or plasma. Both plasmids were spiked into the samples, one plasmid concentration constant (10 fg) using the eight concentrations of the other plasmid. The reverse process was also done. The urine, PBMC, plasma, CSF were obtained from negative healthy donors. No significant changes were observed in amplification efficiency of either variant due to concentration of competing variant or in the presence of DNA extracted from urine, PBMC or CSF. Plasma DNA extraction solution showed some reduced amplification efficiency at 10 ul but none at 5 µl Therefore, in testing plasma samples, both 10 µl and 5 µl concentrations are run to normalize for this possible effect.

Example 2

Multiplex qPCR Assay for Detection of Archetype and Prototype JC Virus

The example illustrates embodiments of a method and compositions for detecting the presence of JC virus in a biological sample, including detecting the presence of Archetype and Prototype JC virus in a biological sample. The JC virus multiplex qPCR assay described herein quantitatively detects viral DNA in clinical samples using one series of primers in the conserved region necessary for viral growth while simultaneously detecting the non-pathogenic/ Archetype variant using primers selected for the NCRR sequences specific to the Archetype variant. The assay also provides a research tool for the identification of the cellular location in which different virus variants maintain latency and where changes from one form to another may occur. Discrimination between the non-pathogenic/Archetype and pathogenic/Prototype JC virus in blood has significant value to patients with compromised immunity who are at risk but have not developed PML.

The genotype of urine excreted virus, considered non-pathogenic, has a unique arrangement of the non-coding regulatory region nucleotide sequences, NCRR, of 268 base pairs. Viral variants with this nucleotide structure, termed the 'Archetype,' have rarely been associated with PML. However, select deletions and duplications in the Archetype NCRR that result in direct tandem repeats may give rise to the arrangement of the pathogenic variant (Jensen and Major, *J Neurovirol.*, 7:280-7, 2001). It is unclear in what tissues or cells such alterations could occur. The most likely candidate sites are lymphoid tissues including the bone marrow in which JC virus can also be latent (Houff et al., *N Engl J Med.* 318: 301-305, 1988; Tan et al., *J. Infect. Dis.*, 199:881-888, 2009).

FIGS. 1A and 1B show the NCRR nucleotide sequence arrangement of the two major variants, Archetype, represented by the urine isolate CY (Yogo et al., *J. Virol.*, 64:3139-43, 1990), and tandem repeat/Prototype, derived from the original isolate of JC virus Mad-1 (Frisque, et al.,

*J. Virol.,* 51:458-69, 1984) from PML brain tissue. The location of the PCR primers and probes for the T protein sequence, JCT, and the NCRR of the Archetype, JRR, are identified in relation to the entire 5.13 kb genome. Both variants have similar T protein coding sequences. Since the region of the genome identified by the T primers/probe is necessary for viral growth, alterations in that region result in non-viable virus. Also, those coding sequences for T protein, just after the splice site for small t, are unique to JC virus so DNA amplification is specific, non-cross-reacting to other human polyomaviruses for either the Prototype or Archetype variants. Consequently, qPCR for the JCT regions provides a measure of the copy number of JC virus DNA regardless of its variant origin (Ryschkewitsch et al., *J Virol Methods.* 121:217-221, 2004). Amplification of viral DNA in CSF samples using the JCT set of primers and probe has proved highly sensitive and specific and is the basis for the laboratory confirmatory diagnostic marker for PML (Ryschkewitsch et al., J Virol Methods. 121:217-221, 2004). For example, of the first 140 cases of PML in MS patients under treatment with the α integrin blocker natalizumab, confirmatory diagnosis using the JCT set of primers was provided in 72 cases.

However, qPCR with JCT primers does not distinguish between the Archetype and the Prototype variants. Direct nucleotide sequencing of recovered viral DNA from the CSF is necessary to make that distinction. Viral DNA can also be present in the blood in non-PML patients which is not surprising for a widely spread DNA virus. Although viremia is not a diagnostic aid for PML, since it can be found in approximately 2% of the general population, it can be a considerable factor in patients with underlying immune compromised conditions (Viscidi, et al., *Clin. Inf. Diseases,* 53: 711-715, 2011). Consequently, the identification of the genotypic variant as pathogenic or non-pathogenic provides value in determining which patients may be at greater risk for developing PML. Other qPCR assays described as multiplex distinguish JC virus from other DNA viruses but cannot distinguish between JC virus variants (such as Archetype and Prototype variants) (Jensen and Major, *J. Leukoc. Biol.,* 65:428-38, 1999).

FIG. 2 shows amplification of a 'standard,' plasmid containing Archetype JC virus DNA (FIG. 2A, FIG. 2B) or Prototype JC virus (FIG. 2C, FIG. 2D) using the qPCR assay with the JCT primers and probes specific for the T region of JC virus (Ryschkewitsch et al., *J Virol Methods.* 121:217-221, 2004) and for NCRR. Since the viral Archetype DNA contains both target DNA sequences, ten-fold serial dilutions of the standard DNA show 'real time' detection of T sequences, black line, with identification of the viral DNA as Archetype, grey line, crossing threshold Ct values at the same cycle (FIG. 2A) and as anticipated in a linear degree (FIG. 2B). Sensitivity of the assay is similar to that achieved with the JCT primers/probe at 10 copies/ml. FIG. 2C shows qPCR amplification of tenfold serial dilutions of the standard, plasmid containing Prototype JC virus DNA spiked with only 10 fg of plasmid containing Archetype JC virus DNA showing detection of only the T sequences in the Prototype variant Ct values through cycle 26 when both Prototype and spiked Archetype DNA are identified. When higher concentrations of Archetype DNA was spiked into each of the dilutions of Prototype DNA (FIG. 2D) then both Prototype and Archetype are detected as expected. At higher Ct values, the T antigen sequences are more numerous, and cross the threshold (black line), before the Archetype (grey line), since 'Prototype only' also adds to total copy number.

Ct values of a clinical sample in which the T antigen sequence copies are greater than any detectable Archetype sequences demonstrate that both genotypic variants are present. Interpretation of amplification from a clinical sample in which no Archetype is detected would predict the presence of the pathogenic variant as in CSF of a PML patient. In laboratory derived 'Archetype only' samples, both T and Archetype would have similar Ct values demonstrating that only Archetype or the non-pathogenic variant is present. However, in testing clinical samples of urines taken from healthy individuals and non-PML patients, the T antigen primer amplification has an average δCt of 1.61 or between 1 and 2 cycles ahead of amplification of Archetype. All urine samples tested as well as serial dilutions of the samples showed this profile. Consequently, in some embodiments, the technical assay limit of distinction in clinical samples between Archetype and Prototype is set at δCt2 (at least two amplification cycles between detection of amplified JC virus DNA using the non-specific primers and detection of amplified JC virus DNA using the Archetype-specific primers).

Figure 3A:
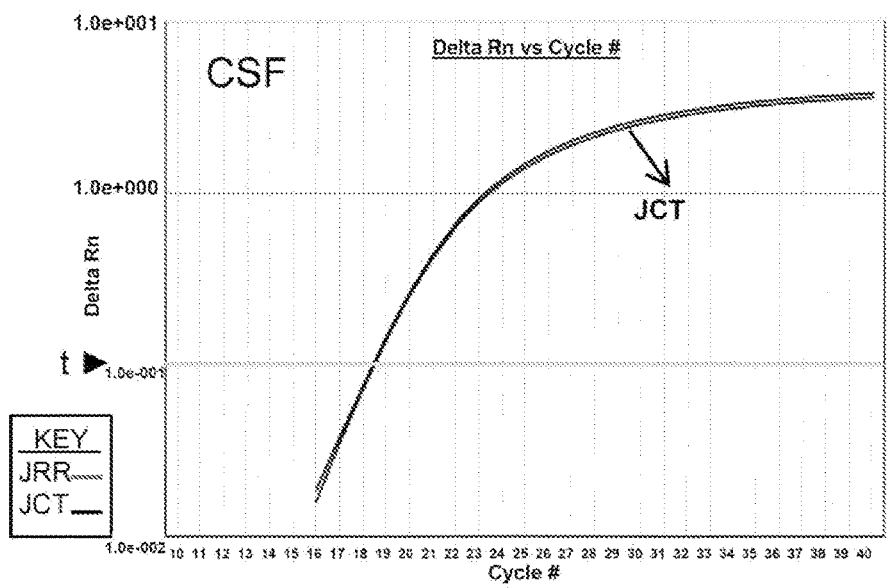
FIGS. 3A-3F are a set of graphs illustrating amplification-plots of multiplex qPCR assays using the JC virus regulatory region primer-set and probe JRR-1, JRR-2, JRR-1.1-VIC (grey; Archetype specific; "JRR"), in addition to the JC virus large-T antigen primer-set and probe JCT-3, JCT-4, JCT-1.2-FAM (black; non-specific; "JCT") and total DNA extracted from 200 µl for each of three matched PML patient samples: CSF (FIG. 3A), plasma (FIG. 3B) and urine (FIG. 3C) from an HIV-1/AIDS patient with PML, and CSF (FIG. 3D), plasma (FIG. 3E) and urine (FIG. 3F) from a natalizumab treated multiple sclerosis patient with PML. The threshold (t) was set at a consistent Delta Rn level and falls appropriately in the geometric phase for each these amplifications. These amplification-plots represent duplicate reactions, with the CSF and plasma run together on one plate and the urine run separately on a second plate. These data show similar patterns to data generated with the same assay on numerous other matched PML patient samples.

FIG. 3 shows the clinical utility of the multiplex assay in two PML patients with different underlying diseases and risk: qPCR amplification of clinical samples from a PML patient with AIDS (FIG. 3A; CSF) only T antigen detection indicating presence of the pathogenic variant (FIG. 3B; plasma) sample taken close to time of PML diagnosis indicating the presence of only the pathogenic variant and (FIG. 3C; urine) sample taken close to time of PML diagnosis with high copies of the Archetype with T showing a δCt 2. An identical profile was seen in samples from a natalizumab treated MS/PML patient in the CSF (FIG. 3D), plasma (FIG. 3E), and urine (FIG. 3F).

This distribution of variant forms of JC virus DNA is not unique to PML patients with severe immune suppressive underlying diseases such as AIDS. In another set of samples from an MS patient on natalizumab treatment who developed PML after 20 infusions, there was a near identical distribution of viral DNA.

In other MS patients from whom blood samples were available prior to or around the time of suspicion of PML, both the pathogenic/Prototype variant and to a much lesser extent the non-pathogenic/Archetype variant were evident in the plasma. For example, a serum sample taken before the confirmatory diagnosis of PML shows a predominance of the pathogenic/Prototype variant with just detectable levels of the non-pathogenic/Archetype variant. After PML confirmation based on clinical symptoms, MRI evidence and JC virus DNA in the CSF, the serum shows only pathogenic/Prototype variant similar to the data in FIG. 3.

Figure 3B:
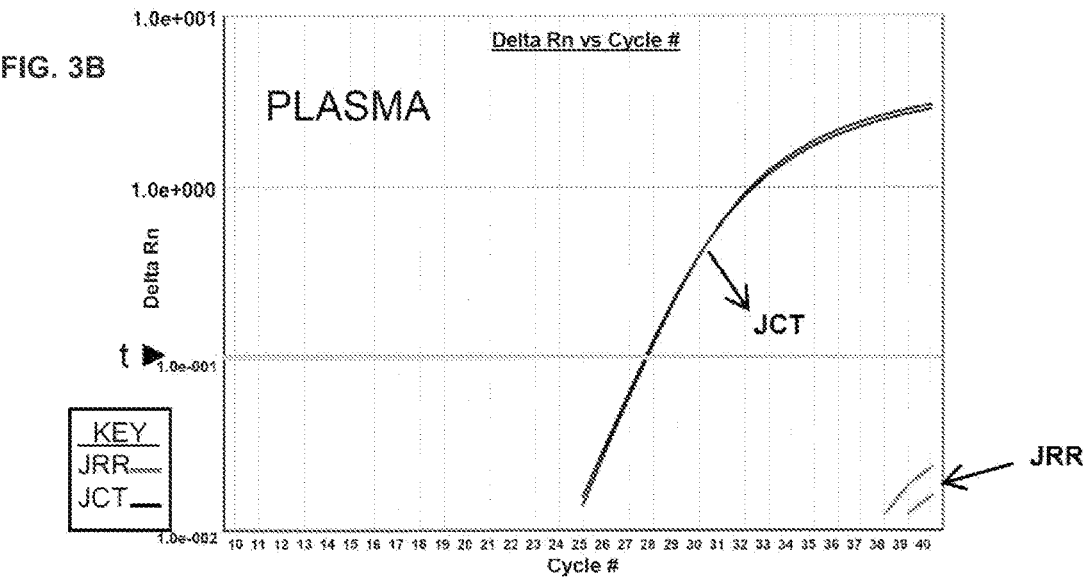
Figure 3C:
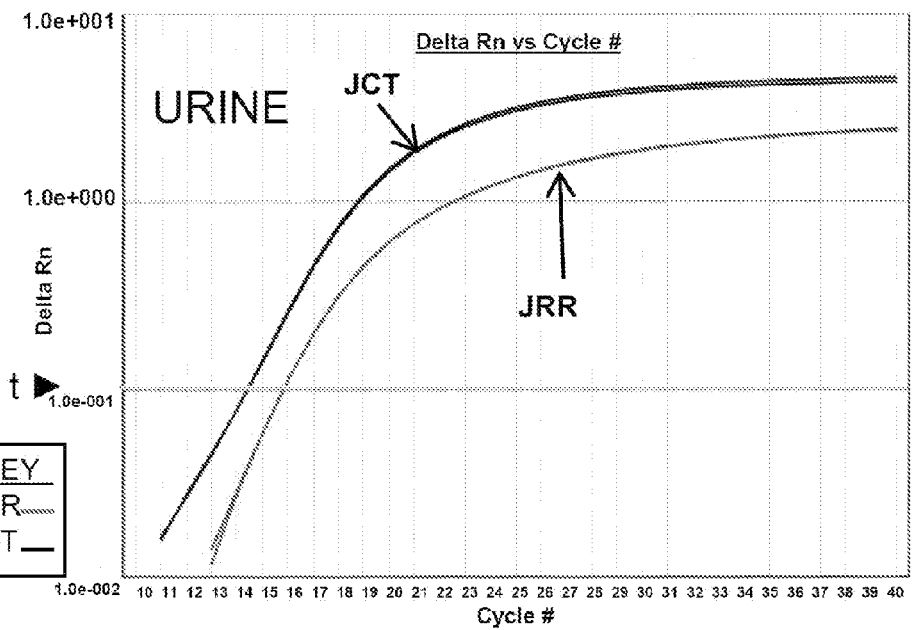
Figure 3D:
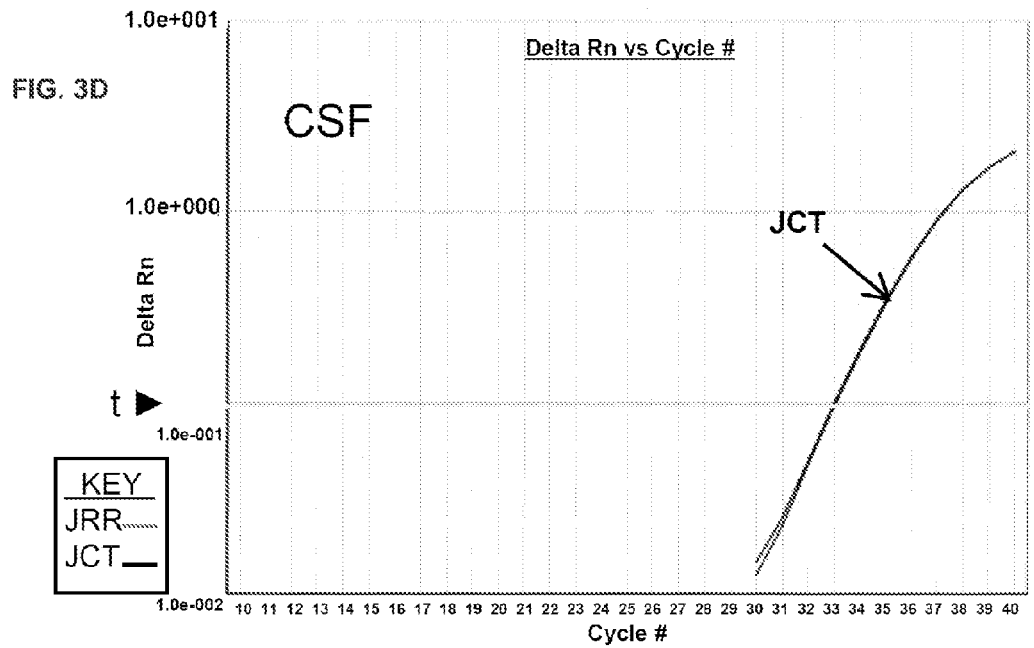
Figure 3E:
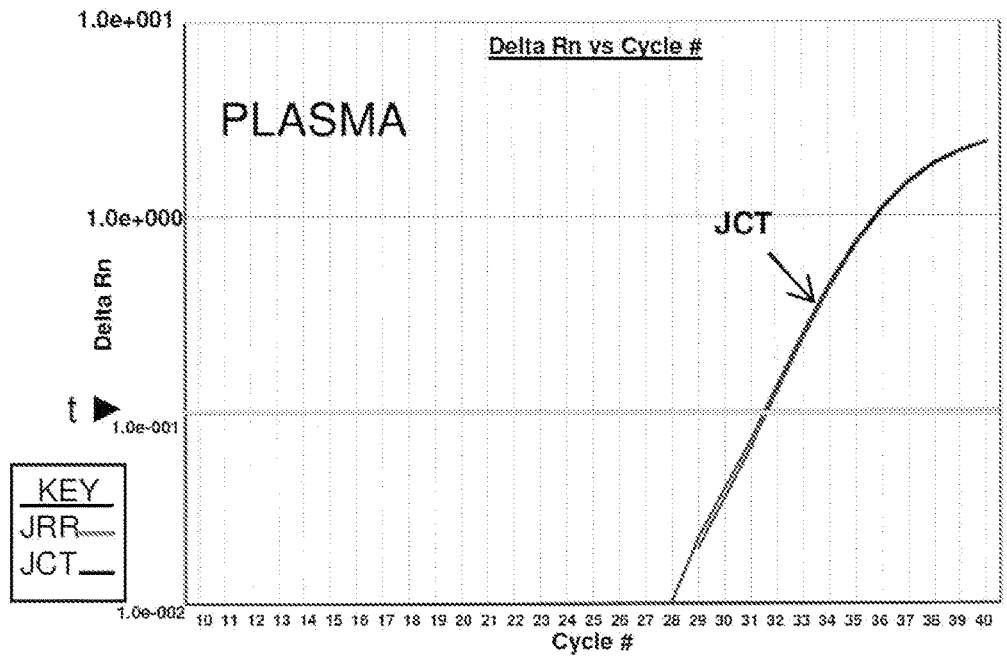
Figure 3F:
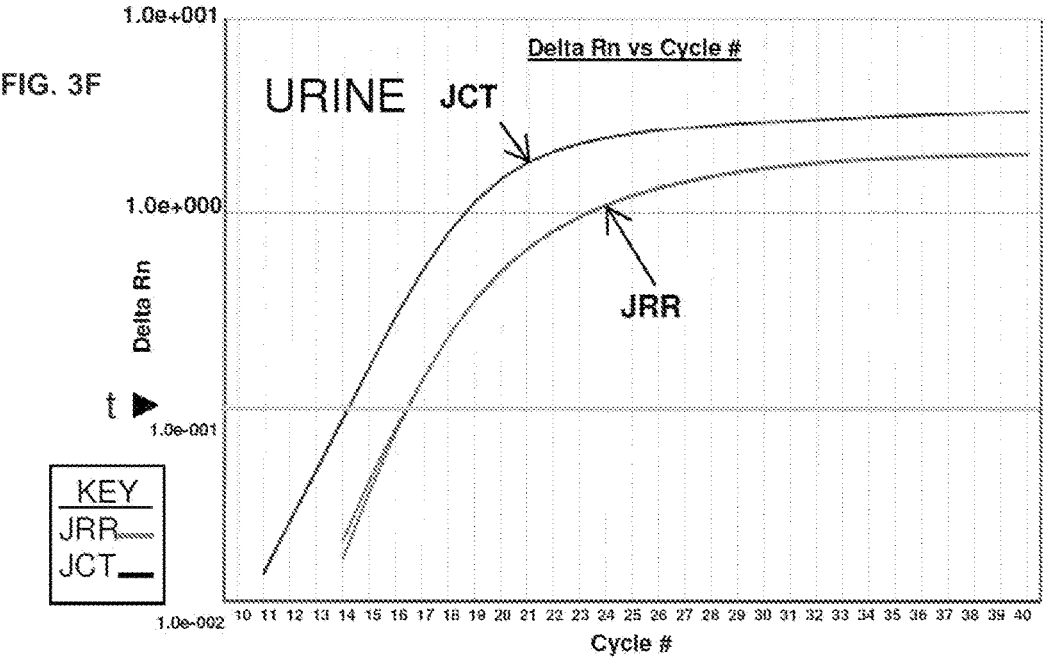

Current qPCR assays, including the Clinical Laboratory Improvement Amendment (CLIA) validated/certified assay described herein, target the conserved T protein coding sequence that identifies the presence of JC virus DNA regardless of any nucleotide variations located in other regions of the viral genome. The assay provided herein is very sensitive and specific: 10 copies/ml of plasma or CSF using the Qiagen DNA spin column kit for template extraction (Ryschkewitsch et al., *Ann, Neurol.,* 68:384-91, 2010). The simultaneous detection of an additional target sequence in the Archetype NCRR using the same template adds a new dimension to the qPCR assay as a multiplex assay. The Archetype variant is not associated with pathological consequences of JC virus infection and considered not the variant that causes PML (Jensen and Major, *J. Leukoc. Biol.,* 65:428-38, 1999; Agostini et al., *Res. Virol.,* 149:163-170, 1998). Therefore its identification in plasma/serum, PBMCs, or other tissues does not carry the same risk for PML as would the Prototype variant. The provided multiplex assay then discriminates between the non-pathogenic/Archetype and pathogenic/Prototype variants by either detecting the Archetype alone or by detecting viral DNA that does not have the Archetype genotype. For example, if a plasma sample has detectable copies of viral DNA measured by the amplification on the T region but does not detect the Archetype DNA, then the sample is related to the Prototype/ pathogenic variant. This is what is shown in FIG. 3B from a PML patient. If the plasma sample was taken from a non-PML patient with an underlying disease or therapy that has a risk for PML, then the presence of the pathogenic/ Prototype variant in the circulation would be considered an additional risk for PML. The JC virus DNA multiplex assay provides this information from PCR analysis of the same template in one assay format down to the level of δCt2 between T and Archetype primers/probe. One non-limiting example of the utility of the multiplex assay is the testing of urine and/or plasma samples over time from patients in risk categories e.g., immune compromised conditions. Any increase in the presence of T antigen sequences over Archetype above δCt2 would indicate the multiplication of the pathogenic/Prototype and not the non-pathogenic/Archetype JC virus variant indicating a greater risk for the potential development of PML.

Example 3

Optimizing Primers for Amplifying JC Virus Sequences

Figure 4:
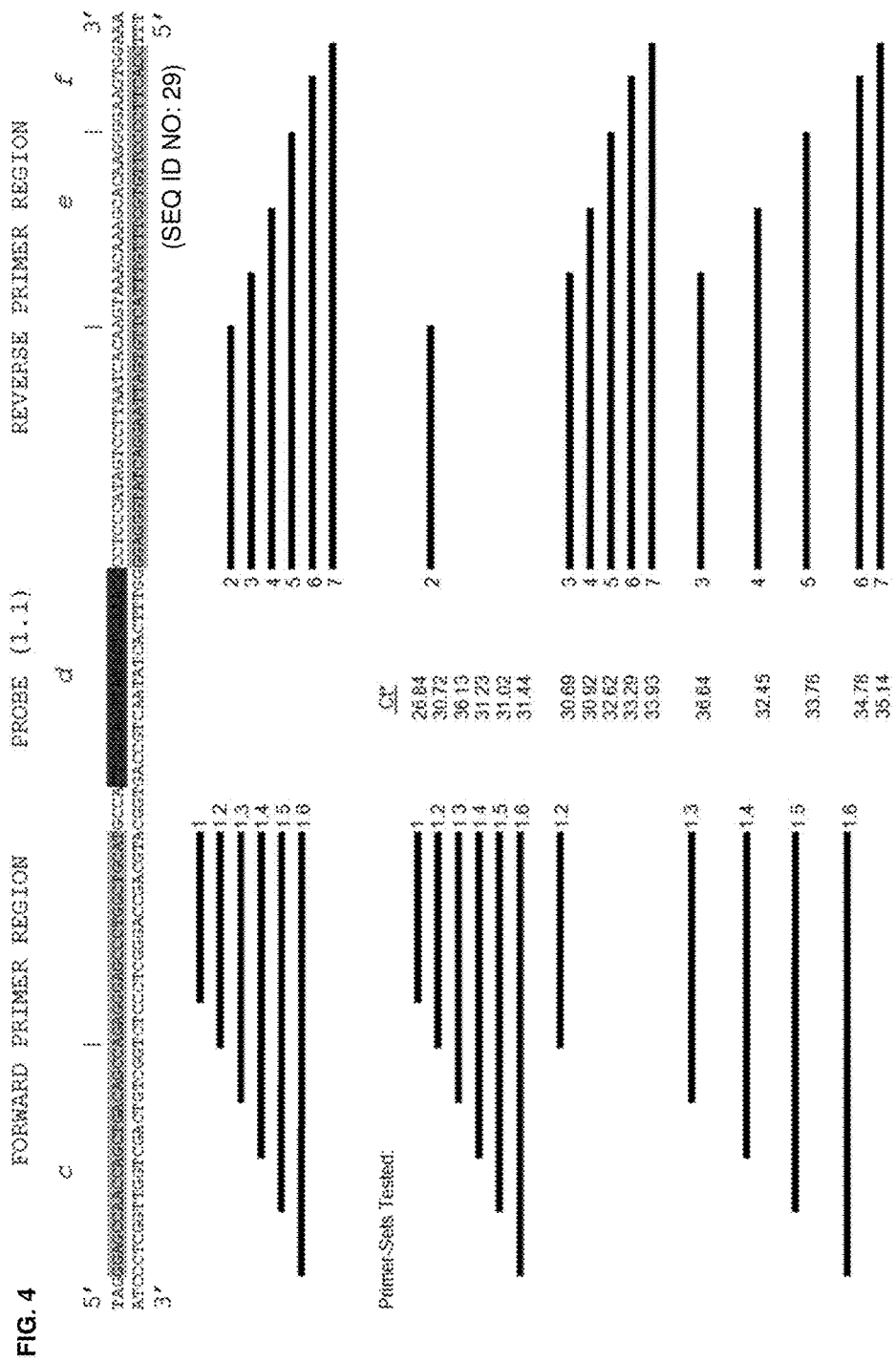
FIG. 4 is a schematic diagram illustrating a panel of primers for amplifying and detecting JC virus with the d section of the hypervariable region of the NCRR specific to Archetype JC virus. The nucleotide sequence of part of the hypervariable regions of the NCRR (including the d section) of Archetype JC virus (nucleotides 91-209 of the SEQ ID NO: 1) is shown. The forward and reverse primers tested are shown graphically. The regions of the Archetype JC virus sequence encompassing the forward and reverse primers are highlighted, as is the region of the d section of the Archetype NCRR used for the oligonucleotide probe in the qPCR assays (probe JRR1.1 was used). The amplification cycle point value for when the amplified qPCR product crossed the threshold value (Ct) for each set of primer is shown. All reactions were performed under identical conditions.

This example illustrates the optimization of oligonucleotide primers for use in a qPCR assay to amplify and detect the Archetype-specific hypervariable region sequences. The panel of forward and reverse oligonucleotide primers is illustrated in FIG. 4 and listed in Table 3. The primer pairs tested are shown in FIG. 4. The oligonucleotide probe used for the qPCR assays was JRR1.1. The conditions for the qPCR assays used to test the various forward and reverse primer pairs were performed as described above for assays using the JRR1/JRR2/JRR1.2 set of primers and probes. All reactions were performed under identical conditions. The amplification cycle point value for when the amplified qPCR product crossed the threshold value (Ct) for each set of primer is shown. Note that the Ct value shown in FIG. 4 can be to identify PCR reactions that generated amplified product, and for comparison of the relative efficiency of the reactions under the selected conditions (which were optimized for PCR using the JRR1 and JRR2 primers), but may not be an indicator of the efficiency of the reactions run under different conditions.

In view of the many possible embodiments to which the principles of the disclosure may be applied, it should be recognized that illustrated embodiments are only examples and should not be considered a limitation on the scope of the claims. We therefore claim all that comes within the scope and spirit of these claims.

We claim:

1. A method of detecting the presence or absence of Prototype JC virus in a biological sample from a subject, comprising:

amplifying and detecting an amount of a first nucleic acid molecule and an amount of a second nucleic acid molecule from the biological sample using a using a multiplex quantitative real-time polymerase chain reaction (qPCR) assay, comprising:

amplifying the first nucleic acid molecule with a first oligonucleotide primer pair comprising forward and reverse oligonucleotide primers consisting essentially of the nucleotide sequences set forth as SEQ ID NOs: 3 (JRR-1) and 4 (JRR-2), respectively;

detecting the amplified first nucleic acid molecule with a first oligonucleotide probe consisting essentially of the nucleotide sequence set forth as SEQ ID NO: 5 (JRR-1.1), or the complement thereof;

amplifying the second nucleic acid molecule with a second oligonucleotide primer pair comprising forward and reverse oligonucleotide primers consisting essentially of nucleotide sequences set forth as SEQ ID NOs: 6 (JCT-3) and 7 (JCT-4), respectively;

detecting the amplified second nucleic acid molecule with a second oligonucleotide probe consisting essentially of the nucleotide sequence set forth as SEQ ID NO: 8 (JCT-1.2), or the complement thereof; and wherein the first nucleic acid molecule is present in an Archetype JC virus genome but not the Prototype JC virus genome, and the second nucleic acid molecule is present in both the Archetype and Prototype JC virus genomes;

detecting a greater amount of the second nucleic acid molecule than the first nucleic acid molecule in the biological sample identifies the presence of Prototype JC virus in the biological sample; and detecting an equal amount of the first and second nucleic acid molecules in the biological sample identifies the absence of Prototype JC virus in the biological sample.

2. The method of claim 1, wherein the forward and reverse oligonucleotide primers of the first oligonucleotide pair consist of the nucleotide sequences set forth as SEQ ID NOs: 3 and 4, respectively; and the forward and reverse oligonucleotide primers of the second oligonucleotide pair consist of the nucleotide sequences set forth as SEQ ID NOs: 6 and 7, respectively.

3. The method of claim 1, wherein the subject is a subject at risk of developing progressive multifocal leukoencephalopathy (PML).

4. The method of claim 3, wherein subject is an immunocompromised subject.

5. The method of claim 3, wherein the subject has an HIV infection or multiple sclerosis.

6. The method of claim 5, wherein the subject has AIDS.

7. The method of claim 3, wherein the subject is being treated with an immunosuppressive therapy.

8. The method of claim 7, wherein the subject is being treated with natalizumab.

9. The method of claim 1, wherein the biological sample is a cerebrospinal fluid (CSF), blood or urine sample.

10. The method of claim 1, wherein detecting the presence of Prototype JC virus in the biological sample identifies the subject as having an increased risk of developing progressive multifocal leukoencephalopathy (PML).

11. The method of claim 10, further comprising inhibiting PML in the subject, comprising administering to the subject a therapeutically effective amount of an anti-PML agent, thereby inhibiting PML in the subject.

12. The method of claim 11, wherein the anti-PML agent is cytosine arabinoside or cidofovir.

13. A composition, comprising:
a first oligonucleotide primer pair comprising forward and reverse oligonucleotide primers consisting essentially of the nucleotide sequences set forth as SEQ ID NOs: 3 and 4, respectively; and
a first oligonucleotide probe consisting essentially of the nucleotide sequence set forth as SEQ ID NO: 5, or the complement thereof, wherein the first oligonucleotide probe is labeled with a detectable marker.

14. The composition of claim 13, wherein the forward and reverse oligonucleotide primers of the first oligonucleotide primer pair consist of the nucleotide sequences set forth as SEQ ID NOs: 3 and 4, respectively.

15. The composition of claim 13, further comprising:
a second oligonucleotide primer pair comprising forward and reverse oligonucleotide primers consisting essentially of the nucleotide sequences set forth as SEQ ID NOs: 6 and 7, respectively; and
a second oligonucleotide probe consisting essentially of the nucleotide sequence set forth as SEQ ID NO: 8, or the complement thereof; wherein the second oligonucleotide probe is labeled with a detectable marker that is different from the detectable marker of the first oligonucleotide probe.

16. The composition of claim 15, wherein
the forward and reverse oligonucleotide primers of the first oligonucleotide primer pair consist of the nucleotide sequences set forth as SEQ ID NOs: 3 and 4, respectively; and
the forward and reverse oligonucleotide primers of the second oligonucleotide primer pair consist of the nucleotide sequences set forth as SEQ ID NOs: 6 and 7, respectively.

17. A kit for detecting the presence of Prototype and/or Archetype JC virus in a biological sample from a subject, comprising:
a container comprising the composition of claim 13; and
instructions for using the kit.

18. A kit for detecting the presence of Prototype and/or Archetype JC virus in a biological sample from a subject, the kit comprising a set of containers comprising:
a first oligonucleotide primer consisting essentially of the nucleotide sequence set forth as SEQ ID NO: 3;
a second oligonucleotide primer consisting essentially of the nucleotide sequence set forth as SEQ ID NO: 4;
a third oligonucleotide primer consisting essentially of the nucleotide sequence set forth as SEQ ID NO: 6;
a fourth oligonucleotide primer consisting essentially of the nucleotide sequence set forth as SEQ ID NO: 7;
a first oligonucleotide probe consisting essentially of the nucleotide sequence set forth as SEQ ID NO: 5, or the complement thereof;
a second oligonucleotide probe consisting essentially of the nucleotide sequence set forth as SEQ ID NO: 8, or the complement thereof; and
wherein the first and second oligonucleotide probes are labeled with different detectable labels.

19. The kit of claim 18, wherein the first, second, third, and fourth oligonucleotide primers consist of the nucleotide sequences set forth as SEQ ID NOs: 3, 4, 6, and 7, respectively.

* * * * *

SEQUENCE LISTING

```
<160> NUMBER OF SEQ ID NOS: 29

<210> SEQ ID NO 1
<211> LENGTH: 5120
<212> TYPE: DNA
<213> ORGANISM: JC virus

<400> SEQUENCE: 1
gcctcggcct cctgtatata taaaaaaaag ggaaggtagg gaggagctgg ctaaaactgg      60
atggctgcca gccaagcatg agctcatacc tagggagcca accagctgac agccagaggg     120
agccctggct gcatgccact ggcagttata gtgaaacccc tcccatagtc cttaatcaca     180
agtaaacaaa gcacaagggg aagtggaaag cagccagggg aacatgtttt gcgagccaga     240
gctgttttgg cttgtcacca gctggccatg gttcttcgcc agctgtcacg taaggcttct     300
gtgaaagtta gtaaaacctg gagtggaact aaaaaaagag ctcaaaggat tttaattttt     360
ttgttagaat ttttgctgga cttttgcaca ggtgaagaca gtgtagacgg gaaaaaaaga     420
cagaaacaca gtggtttgac tgagcagaga tacagtgctt tgcctgaacc aaaagctaca     480
taggtaagta atgttttttt ttgtgttttc aggttcatgg gtgccgcact tgcacttttg     540
ggggacctag ttgctactgt ttctgaggct gctgctgcca caggattttc agtagctgaa     600
attgctgctg gagaggctgc tgctactata gaagttgaaa ttgcatccct tgctactgta     660
gaggggatta caagtacctc tgaggctata gctgctatag gccttactcc tgaaacatat     720
gctgtaatta ctggagctcc gggggctgta gctgggtttg ctgcattggt tcaaactgta     780
```

-continued

```
actggtggta gtgctattgc tcagttggga tatagatttt ttgctgactg ggatcataaa      840
gtttcaacag ttgggctttt tcagcagcca gctatggctt tacagttatt taatccagaa      900
gactactatg atattttatt tcctggagtg aatgcctttg ttaacaatat tcactattta      960
gatcctagac attggggccc ttctttgttc tccacaatct cccaggcttt ttggaaccct     1020
gttagagatg atttgccatc tttaacatct caggaaattc aaagaagaac caaaaacta     1080 tttgttgaaa gtttagcaag ttttttggaa gaaactactg ggcaatagt taattcacca     1140 gttaacttat ataattatat ttcagactat tattctagat tgtctccagt aaggccctct    1200
atggtaaggc aggttgccca aagggaggga acctatattt cctttggcca ctcatacacc    1260
caaagtatag atgatgcaga cagcattcaa gaagttaccc aaaggctaga tttaaaaacc    1320
ccaaatgtgc aatctggtga gtttatagag aaaagtattg caccaggagg tgcaaatcaa    1380
agatctgctc ctcaatggat gttgccttta cttttagggt tgtacgggac tgtaacacct    1440
gctcttgaag catatgaaga tggccccaac aaaaagaaaa ggagaaagga aggacccgt     1500 gcaagttcca aaacttctta taagaggagg agtagaagtt ctagaagtta aaactggggt    1560
tgactcaatt acagaggtag aatgttttt aactccagaa atgggtgacc cagatgagca     1620
tcttaggggt tttagtaagt caatttctat atcagataca tttgaaagtg actccccaaa    1680
taaggacatg cttccttgtt acagtgtggc cagaattcca ctaccaatc taaatgagga     1740 tctaacctgt ggaaatatac taatgtggga ggctgtgacc ttaaaaactg aggttatagg    1800
ggtaacaact ttgatgaatg tgcactctaa tggtcaagca actcatgaca atggtgcagg    1860
aaagccagtg cagggcacca gctttcattt tttttctgtt gggggggagg ctttagaatt    1920 acaggggtg gttttaact acagaacaaa gtacccagat ggaacaattt ttccaaagaa     1980
tgcaacagtg caatctcaag taatgaacac agagcacaag gcgtacctag ataagaacaa    2040
agcatatcct gttgaatgtt gggttcctga tcccaccaga aatgaaaaca caagatattt    2100
tgggacacta acaggaggag aaaatgttcc tccagttctt catataacaa acactgccac    2160
aacagtgctg cttgatgaat ttggtgttgg gccacttgc aaaggtgaca acttgtattt     2220
gtcagctgtg gatgtttgtg gcatgtttac taacagatct ggttcccagc agtggagagg    2280
actgtccaga tattttaagg ttcagctaag aaaaaggagg gttaaaaacc cctacccaat    2340
ttcttttcct cttactgatt taattaacag aaggacccct agagttgatg ggcagcctat    2400
gtatggcatg gatgctcagg tagaggaggt tagagttttt gagggaacag aggaacttcc    2460 aggggacccca gacatgatga gatatgttga cagatatgga cagttgcaga caaagatgct    2520
gtaatcaaaa gcctttattg taatatgcag tacattttaa taaagtataa ccagctttac    2580
tttgcagttg cagttacttt ggggagggg ttttggttt tttgaaacat tgaaagcctt      2640
tacagatgtg ataggtgcag tgttcctgtg tgtctgcacc agaggcttct gagacctggg    2700
aagagcattg tgattgagat tcagtgcttg atccatgtcc agagtcttct gcttcagaat    2760
cttcctctct aggaaagtca agaatgggtc tccccatacc aacattagct ttcatagtag    2820
aaaatgtata catgcttatt tctaaatcca gcctttcttt ccactgcaca atcctctcat    2880
gaatggcagc tgcaaagtca gcaactggcc taaaccgat taaaagcaaa agcaaagtca    2940
tgccactttg caaaatcctt ttttctagta atattcaga gcagcttagt gattttctta     3000
ggtaggcctt aggtctaaaa tctatttgcc ttacaaatct ggcttgtaaa gttcaggca    3060 ctgaatattc attcatggtt acaattccag gtggaaacac ctgtgttctt ttgttttggt    3120
```

```
gttttctctc taaattaact ttcacacttc catctaagta atctcttagg caatcaaggt    3180
tgcttatgcc atgccctgaa ggtaaatccc ttgactctgc accagtgcct tttacatcct    3240
caaatacaac cataaactga tctatacccca ctcctaactc aaagtttaat ctttctaatg    3300
gcatattaac atttaatgac tttcccccac agagatcaag taaagctgca gctaaagtag    3360
ttttgccact gtctattggc cccttgaata gccagtacct ttttttttgga atgtttaata    3420
caatgcattt taagaactca taaatgactg tgtccatttg aggcagcaaa caatgaatcc    3480
aggccacccc agccatatat tgctctaaaa cagcattgcc atgtgcccca aaaattaagt    3540
ccattttatc aagcaaaaaa ttaaaccttt caactaacat ttcttctctg gtcatatgga    3600
gactgtcaac cctttgtttg gctgctacag tatcaacagc ctgctggcaa atgcttttt     3660
gattttttgct atctgcaaaa atttgggcat tataatagtg cttttcatga tggttaaagt    3720
gatttggctg atccttcttt tcacattttt tgcattgcag tgggttttcc tgaaagttta    3780
agtacatgcc cataagcaag aaaacatcct cacacttggt gtccaaagca tactgtgtaa    3840
ctaatttcca tgaaacctgc ttagtttctt ctggttcttc tgggttaaag tcatgctcct    3900
taaggccccc ctgaatactt tcttccacta ctgcatatgg ctgtctacac aaggcactgt    3960
aaaacaagta ttccttattc acacctttac aaattaaaaa actaaaggta catagtttct    4020
gacagtaatt attaattgct gaaactctat gtctatgtgg tgttaaaaaa aacaaaatat    4080
tatgacccccc aaaaccatgt ctacttataa aggttacaga atattttttcc ataagtttct    4140
tatataaaat ttgagctttt tctttagtgg tatacacagc aaaagaagca acagttctat    4200
tactaaacac agcttgactg aggaatgcat gcagatctac aggaaagtct ttagggtctt    4260
ctacctttttt tttctcttctta ggtggggtag agtgttggga tcctgtgttt tcatcatcac    4320
tggcaaacat ttcttcatgg caaaacaggt cttcatccca cttctcatta aatgtattcc    4380
accaggattc ccactcatct gttccatagg ttggcaccta aaaacaaaaa attcagttta    4440
tgtaaaaaac aaaatgccct gcaaaagaaa aattgtggtt taccttaaag ctttagatcc    4500
ctgtaggggg tgtctccaag aaccttctcc cagcaatgaa gagcttcttg ggttaagtca    4560
cacccaaacc attgtctgaa gcaatcaaag caatagcaat ctatccacac aagtgggctg    4620
cttcttaaaa atttctgtt tctatgcctt aattttagca tgcacattaa acagggcaa     4680
tgcactgaag gattagtggc acaattaggc cattccttgc aataaagagt atcagaatta    4740
ggaggaaaat cacaaccaac ctctgaacta ttccatgtac caaaatcagg ctgatgagca    4800
acttttacac cttgttccat ttttttatat aaaaagttca ttctcttcat tttgtcttcg    4860
tccccacctt tatcagggtg aagttctttg cattttttca gataagcttt tctcatgaca    4920
ggaatgtttc cccatgcaga tctatcaagg cctaataaat ccatgagctc catggattcc    4980
tccctattca gcactttgtc cattttttgct ttttgtagca aaaaattagt gcaaaaagg    5040
gaaaaacaag ggaatttccc tggcctccta aaaagcctcc acgcccttac tacttctgag    5100
taagcttgga ggcggaggcg                                                5120
```

<210> SEQ ID NO 2
<211> LENGTH: 5130
<212> TYPE: DNA
<213> ORGANISM: JC virus
<400> SEQUENCE: 2

```
gcctcggcct cctgtatata taaaaaaaag ggaagggatg gctgccagcc aagcatgagc      60
tcatacctag ggagccaacc agctaacagc cagtaaacaa agcacaaggc tgtatatata     120
```

```
aaaaaaaggg aagggatggc tgccagccaa gcatgagctc atacctaggg agccaaccag     180
ctaacagcca gtaaacaaag cacaagggga agtggaaagc agccaaggga acatgttttg     240
cgagccagag ctgttttggc ttgtcaccag ctggccatgg ttcttcgcca gctgtcacgt     300
aaggcttctg tgaaagttag taaaacctgg agtggaacta aaaaaagagc tcaaaggatt     360 ttaattttt tgttagaatt tttgctggac ttttgcacag gtgaagacag tgtagacggg     420
aaaaaaagac agagacacag tggtttgact gagcagacat acagtgcttt gcctgaacca     480
aaagctacat aggtaagtaa tgttttttt tgtgttttca ggttcatggg tgccgcactt     540
gcacttttgg gggacctagt tgctactgtt tctgaggctg ctgctgccac aggattttca     600
gtagctgaaa ttgctgctgg agaggctgct gctactatag aagttgaaat tgcatccctt     660
gctactgtag aggggattac aagtacctct gaggctatag ctgctatagg ccttactcct     720
gaaacatatg ctgtaataac tggagctccg ggggctgtag ctgggtttgc tgcattggtt     780
caaactgtaa ctggtggtag tgctattgct cagttgggat atagattttt tgctgactgg     840
gatcataaag tttcaacagt tgggcttttt cagcagccag ctatggcttt acaattattt     900
aatccagaag actactatga tattttattt cctggagtga atgcctttgt taacaatatt     960
cactatttag atcctagaca ttggggcccg tccttgttct ccacaatctc ccaggctttt    1020
tggaatcttg ttagagatga tttgccagcc ttaacctctc aggaaattca gagaagaacc    1080
caaaaactat ttgttgaaag tttagcaagg ttttt ggaag aaactacttg ggcaatagtt    1140
aattcaccag ctaacttata taattatatt tcagactatt attctagatt gtctccagtt    1200
aggccctcta tggtaaggca agttgcccaa agggagggaa cctatatttc ttttggccac    1260
tcatacaccc aaagtataga tgatgcagac agcattcaag aagttaccca aaggctagat    1320 ttaaaaccc caaatgtgca atctggtgaa tttatagaaa gaagtattgc accaggaggt    1380
gcaaatcaaa gatctgctcc tcaatgcatg ttgcctttac ttttagggtt gtacgggact    1440
gtaacacctg ctcttgaagc atatgaagat ggccccaaca aaaagaaaag gagaaaggaa    1500
ggaccccgtg caagttccaa aacttcttat aagaggagga gtagaagttc tagaagttaa    1560
aactggggtt gactcaatta cagaggtaga atgctttta actccagaaa tgggtgaccc    1620
agatgagcat cttagggggtt ttagtaagtc aatatctata tcagatacat ttgaaagtga    1680
ctccccaaat agggacatgc ttccttgtta cagtgtggcc agaattccac tacccaatct    1740
aaatgaggat ctaacctgtg gaaatatact catgtgggag ctgtgacct taaaaactga    1800 ggttataggg gtgacaagtt tgatgaatgt gcactctaat gggcaagcaa ctcatgacaa    1860
tggtgcaggg aagccagtgc agggcaccag ctttcatttt ttttctgttg gggggaggc    1920 tttagaatta caggggtgc ttttaatta cagaacaaag tacccagatg gaacaattttt    1980 tccaaagaat gccacagtgc aatctcaagt catgaacaca gagcacaagg cgtacctaga    2040
taagaacaaa gcatatcctg ttgaatgttg ggttcctgat cccaccagaa atgaaaacac    2100
aagatatttt gggacactaa caggaggaga aaatgttcct ccagttcttc atataacaaa    2160
cactgccaca acagtgttgc ttgatgaatt tggtgttggg ccactttgca aggtgacaa    2220 cttatacttg tcagctgttg atgtctgtgg catgttaca acaggtctg gttcccagca    2280 gtggagagga ctctccagat attttaaggt gcagctaagg aaaaggaggg ttaaaaaccc    2340
ctacccaatt tctttтcсttc ttactgattt aattaacaga aggactccta gagttgatgg    2400
gcagcctatg tatggcatgg atgctcaagt agaggaggtt agagttttg agggaacaga    2460
```

-continued

```
ggagcttcca ggggacccag acatgatgag atacgttgac aaatatggac agttgcagac    2520
aaaaatgctg taatcaaaag cctttattgt aatatgcagt acattttaat aaagtataac    2580
cagctttact taacagttgc agttattttg ggggaggggt ctttggtttt ttgaaacatt    2640
gaaagccttt acagatgtga aaagtgcagt tttcctgtgt gtctgcacca gaggcttctg    2700
agacctggga aaagcattgt gattgtgatt cagtgcttga tccatgtcca gagtcttctg    2760
cttcagaatc ttcctctcta ggaaagtcaa gaatgggtct ccccatacca acattagctt    2820
tcatagtaga aaatgtatac atgcttattt ctaaatccag cctttctttc cactgcacaa    2880
tcctctcatg aatggcagct gcaaagtcag caactggcct aaaccagatt aaaagcaaaa    2940
gcaaagtcat accactttgc aaaatccttt tttctagcaa atactcagag cagcttagtg    3000
attttctcag gtaggccttt ggtctaaaat ctatctgcct tacaaatctg gcctgtaaag    3060
ttctaggcac tgaatattca ttcatggtta caattccagg tggaaacacc tgtgttcttt    3120
tgttttggtg ttttctctct aaattaactt ttacacttcc atctaagtaa tctcttaagc    3180
aatcaaggtt gctatgcca tgccctgaag gtaaatccct tgactctgca ccagtgcctt    3240
ttacatcctc aaatacaacc ataaactgat ctatacccac tcctaattca aagtttaatc    3300
tttctaatgg catattaaca tttaatgact ttcccccaca gagatcaagt aaagctgcag    3360
ctaaagtagt tttgccactg tctattggcc ccttgaatag ccagtacctt ttttttggaa    3420
tgtttaatac aatgcatttt agaaagtcat aaataacagt gtccatttga ggcagcaagc    3480
aatgaatcca ggccaccca gccatatatt gctctaaaac agcattgcca tgtgccccaa    3540
aaattaagtc catttatca agcaagaaat taaacctttc aactaacatt tcttctctgg    3600
tcatgtggat gctgtcaacc ctttgtttgg ctgctacagt atcaacagcc tgctggcaaa    3660
tgcttttttg attttgcta tctgcaaaaa tttgggcatt ataatagtgt ttttcatgat    3720
ggttaaagtg atttggctga tcctttttt cacattttt gcattgctgt gggttttcct    3780
gaaagtctaa gtacatgccc ataagcaaaa aaacatcctc acacttggtt tccaaggcat    3840
actgtgtaac taatttccat gaaacctgct tagtttcttc tggttcttct gggttaaagt    3900
catgctcctt aaggccccc tgaatacttt cttccactac tgcatatggc tgtctacaca    3960
gggcactata aaacaagtat tccttattca caccttaca aattaaaaaa ctaaaggtac    4020
atagttttg acagtagtta ttaattgctg acactctatg tctatgtggt gttaagaaaa    4080
acaaaatatt atgaccccca aaaccatgtc tacttataaa agttacagaa tattttccaa    4140
taagtttctt atataaaatt tgagcttttt ctttagtggt atacacagca aaagaagcaa    4200
cagttctatt actaaacaca gcttgactga ggaatgcatg cagatctaca ggaaagtctt    4260
tagggtcttc tacctttttt ttcttttag gtgggtaga gtgttgggat cctgtgtttt    4320
catcatcact ggcaaacatt tcttcatggc aaaacaggtc ttcatcccac ttctcattaa    4380
atgtattcca ccaggattcc cattcatctg ttccataggt tggcacctaa aaaaaaacaa    4440
ttaagtttat tgtaaaaaac aaaatgccct gcaaagaaaa aatagtggtt taccttaaag    4500
ctttagatcc ctgtaggggg tgtctccaag aactttctcc cagcaatgaa gagcttcttg    4560
ggttaagtca cacccaaacc attgtctgaa gcaatcaaag caatagcaat ctatccacac    4620
aagtgggctg cttcttaaaa attttctgtt tctatgcctt aatttagca tgcacattaa    4680
acaggggcaa tgcactgaag gattagtggc acagttaggc cattccttgc aataaagggt    4740
atcagaatta ggaggaaaat cacaaccaac ctctgaacta ttccatgtac caaaatcagg    4800
ctgatgagca acttttacac cttgttccat ttttttatat aaaaaattca ttctcttcat    4860
```

```
cttgtcttcg tccccacctt tatcagggtg gagttctttg catttttca gataagcttt      4920 tctcatgaca ggaatgttcc cccatgcaga cctatcaagg cctaataaat ccataagctc      4980
catggattcc tccctattca gcactttgtc catttagct ttttgcagca aaaaattact       5040
gcaaaaaagg gaaaaacaag ggaatttccc tggcctccta aaaagcctcc acgcccttac      5100
tacttctgag taagcttgga ggcggaggcg                                       5130
```

<210> SEQ ID NO 3
<211> LENGTH: 16
<212> TYPE: DNA
<213> ORGANISM: JC virus

<400> SEQUENCE: 3

```
ggagccctgg ctgcat                                                      16
```

<210> SEQ ID NO 4
<211> LENGTH: 22
<212> TYPE: DNA
<213> ORGANISM: JC virus

<400> SEQUENCE: 4

```
tgtgattaag gactatggga gg                                               22
```

<210> SEQ ID NO 5
<211> LENGTH: 20
<212> TYPE: DNA
<213> ORGANISM: JC virus

<400> SEQUENCE: 5

```
ctggcagtta tagtgaaacc                                                  20
```

<210> SEQ ID NO 6
<211> LENGTH: 23
<212> TYPE: DNA
<213> ORGANISM: JC virus

<400> SEQUENCE: 6

```
agtgttggga tcctgtgttt tca                                              23
```

<210> SEQ ID NO 7
<211> LENGTH: 22
<212> TYPE: DNA
<213> ORGANISM: JC virus

<400> SEQUENCE: 7

```
gtgggatgaa gacctgtttt gc                                               22
```

<210> SEQ ID NO 8
<211> LENGTH: 16
<212> TYPE: DNA
<213> ORGANISM: JC virus

<400> SEQUENCE: 8

```
catcactggc aaacat                                                      16
```

<210> SEQ ID NO 9
<211> LENGTH: 25
<212> TYPE: DNA
<213> ORGANISM: JC virus

<400> SEQUENCE: 9
ctgtatatat aaaaaaaagg gaagg                                              25

<210> SEQ ID NO 10
<211> LENGTH: 23
<212> TYPE: DNA
<213> ORGANISM: JC virus

<400> SEQUENCE: 10
tagggaggag ctggctaaaa ctg                                                23

<210> SEQ ID NO 11
<211> LENGTH: 55
<212> TYPE: DNA
<213> ORGANISM: JC virus

<400> SEQUENCE: 11
gatggctgcc agccaagcat gagctcatac ctagggagcc aaccagctga cagcc            55

<210> SEQ ID NO 12
<211> LENGTH: 66
<212> TYPE: DNA
<213> ORGANISM: JC virus

<400> SEQUENCE: 12
agagggagcc ctggctgcat gccactggca gttatagtga aacccctccc atagtcctta      60
atcaca                                                                  66

<210> SEQ ID NO 13
<211> LENGTH: 18
<212> TYPE: DNA
<213> ORGANISM: JC virus

<400> SEQUENCE: 13
agtaaacaaa gcacaagg                                                     18

<210> SEQ ID NO 14
<211> LENGTH: 69
<212> TYPE: DNA
<213> ORGANISM: JC virus

<400> SEQUENCE: 14
ggaagtggaa agcagccagg ggaacatgtt ttgcgagcca gagctgtttt ggcttgtcac      60
cagctggcc                                                               69

<210> SEQ ID NO 15
<211> LENGTH: 55
<212> TYPE: DNA
<213> ORGANISM: JC virus

<400> SEQUENCE: 15
gatggctgcc agccaagcat gagctcatac ctagggagcc aaccagctaa cagcc            55

<210> SEQ ID NO 16
<211> LENGTH: 39
<212> TYPE: DNA
<213> ORGANISM: JC virus

<400> SEQUENCE: 16
agtaaacaaa gcacaagggg aagtggaaag cagccaagg                              39

<210> SEQ ID NO 17
<211> LENGTH: 48

```
<212> TYPE: DNA
<213> ORGANISM: JC virus

<400> SEQUENCE: 17
gaacatgttt tgcgagccag agctgttttg gcttgtcacc agctggcc                48

<210> SEQ ID NO 18
<211> LENGTH: 24
<212> TYPE: DNA
<213> ORGANISM: JC virus

<400> SEQUENCE: 18
agagggagcc ctggctgcat gcca                                          24

<210> SEQ ID NO 19
<211> LENGTH: 29
<212> TYPE: DNA
<213> ORGANISM: JC virus

<400> SEQUENCE: 19
cagccagagg gagccctggc tgcatgcca                                     29

<210> SEQ ID NO 20
<211> LENGTH: 34
<212> TYPE: DNA
<213> ORGANISM: JC virus

<400> SEQUENCE: 20
gctgacagcc agagggagcc ctggctgcat gcca                               34

<210> SEQ ID NO 21
<211> LENGTH: 39
<212> TYPE: DNA
<213> ORGANISM: JC virus

<400> SEQUENCE: 21
aaccagctga cagccagagg gagccctggc tgcatgcca                          39

<210> SEQ ID NO 22
<211> LENGTH: 45
<212> TYPE: DNA
<213> ORGANISM: JC virus

<400> SEQUENCE: 22
ggagccaacc agctgacagc cagagggagc cctggctgca tgcca                   45

<210> SEQ ID NO 23
<211> LENGTH: 20
<212> TYPE: DNA
<213> ORGANISM: JC virus

<400> SEQUENCE: 23
ctggcagtta tagtgaaacc                                               20

<210> SEQ ID NO 24
<211> LENGTH: 27
<212> TYPE: DNA
<213> ORGANISM: JC virus

<400> SEQUENCE: 24
ttacttgtga ttaaggacta tgggagg                                       27

<210> SEQ ID NO 25
```

```
<211> LENGTH: 33
<212> TYPE: DNA
<213> ORGANISM: JC virus

<400> SEQUENCE: 25
ctttgtttac ttgtgattaa ggactatggg agg                              33

<210> SEQ ID NO 26
<211> LENGTH: 40
<212> TYPE: DNA
<213> ORGANISM: JC virus

<400> SEQUENCE: 26
ccttgtgctt tgtttacttg tgattaagga ctatgggagg                       40

<210> SEQ ID NO 27
<211> LENGTH: 45
<212> TYPE: DNA
<213> ORGANISM: JC virus

<400> SEQUENCE: 27
cttccccttg tgctttgttt acttgtgatt aaggactatg ggagg                 45

<210> SEQ ID NO 28
<211> LENGTH: 48
<212> TYPE: DNA
<213> ORGANISM: JC virus

<400> SEQUENCE: 28
ccacttcccc ttgtgctttg tttacttgtg attaaggact atgggagg              48

<210> SEQ ID NO 29
<211> LENGTH: 119
<212> TYPE: DNA
<213> ORGANISM: JC virus

<400> SEQUENCE: 29
tagggagcca accagctgac agccagaggg agccctggct gcatgccact ggcagttata  60
gtgaaacccc tcccatagtc cttaatcaca agtaaacaaa gcacaagggg aagtggaaa  119
```